United States Patent
Harman et al.

(10) Patent No.: US 8,092,394 B2
(45) Date of Patent: Jan. 10, 2012

(54) METHOD AND APPARATUS FOR SAMPLING AND ANALYSIS OF FLUIDS

(75) Inventors: Anthony David Harman, Oxfordshire (GB); John Maclaren Cassells, Cambridgeshire (GB)

(73) Assignee: Microsample Ltd., Cambridgeshire (GB)

( * ) Notice: Subject to any disclaimer, the term of this patent is extended or adjusted under 35 U.S.C. 154(b) by 237 days.

(21) Appl. No.: 11/574,919

(22) PCT Filed: Sep. 13, 2005

(86) PCT No.: PCT/GB2005/003534
§ 371 (c)(1), (2), (4) Date: Mar. 8, 2007

(87) PCT Pub. No.: WO2006/030201
PCT Pub. Date: Mar. 23, 2006

(65) Prior Publication Data
US 2007/0232956 A1 Oct. 4, 2007

(30) Foreign Application Priority Data
Sep. 13, 2004 (GB) .................................. 0420256.0

(51) Int. Cl.
*A61B 5/00* (2006.01)

(52) U.S. Cl. ............... 600/573; 604/164.08; 382/131

(58) Field of Classification Search ............... 600/573
See application file for complete search history.

(56) References Cited

U.S. PATENT DOCUMENTS

| | | | |
|---|---|---|---|
| 4,270,548 A | 6/1981 | Brennan | |
| 4,360,016 A | 11/1982 | Sarrine | |
| 4,441,373 A * | 4/1984 | White | 73/864.02 |
| 4,653,513 A * | 3/1987 | Dombrowski | 600/578 |
| 4,802,493 A | 2/1989 | Maganias | |
| 4,850,973 A * | 7/1989 | Jordan et al. | 604/157 |
| 4,895,147 A * | 1/1990 | Bodicky et al. | 606/182 |
| 4,920,977 A | 5/1990 | Haynes | |
| 4,966,159 A | 10/1990 | Maganias | |
| 5,026,388 A * | 6/1991 | Ingalz | 606/182 |
| 5,099,857 A * | 3/1992 | Baldo et al. | 600/556 |
| 5,231,993 A | 8/1993 | Haber et al. | |

(Continued)

FOREIGN PATENT DOCUMENTS

CN 1562402 1/2005

(Continued)

*Primary Examiner* — Max Hindenburg
*Assistant Examiner* — Renee Danega
(74) *Attorney, Agent, or Firm* — Frommer Lawrence & Haug LLP; Patrick R. Turner

(57) ABSTRACT

A medical device having a housing (2) with a bore (3) and a lancet (1) slidably fitting in the bore. The lancet operates as a positive displacement piston. In a retracted position, in which the lancet is rearwardly displaced along the bore to define a fluid-containing space in the bore forwardly on the lancet tip, the fluid-containing space has a cross-section dimension to allow fluid to be retained therein by surface tension. The device has a seal (6) operable substantially to prevent flow of fluid from the fluid-containing space past the seal means on movement of the lancet. Displacement of the lancet between the puncture and retracted positions provides suction for drawing fluid into and along the fluid-containing space from the forward end of the bore, and/or pressure for expelling fluid from the fluid-containing space via the forward end of the bore. Also disclosed are methods for operating the device.

25 Claims, 19 Drawing Sheets

U.S. PATENT DOCUMENTS

| | | | |
|---|---|---|---|
| 5,368,047 A | 11/1994 | Suzuki et al. | |
| 5,413,006 A | 5/1995 | D'Autry et al. | |
| 5,569,287 A * | 10/1996 | Tezuka et al. | 606/182 |
| 5,647,371 A | 7/1997 | White, Jr. et al. | |
| 5,801,057 A * | 9/1998 | Smart et al. | 436/68 |
| 5,820,562 A | 10/1998 | Hsiao et al. | |
| 5,944,671 A | 8/1999 | White, Jr. | |
| 6,095,988 A | 8/2000 | Doll et al. | |
| 6,156,004 A * | 12/2000 | Tremaine et al. | 604/27 |
| 6,447,482 B1 * | 9/2002 | Rønborg et al. | 604/131 |
| 6,540,762 B1 | 4/2003 | Bertling et al. | |
| 6,605,048 B1 | 8/2003 | Levin et al. | |
| 6,612,111 B1 * | 9/2003 | Hodges et al. | 60/583 |
| 6,673,023 B2 * | 1/2004 | Pflueger | 600/565 |
| 6,823,750 B2 | 11/2004 | Hodges | |
| 6,830,551 B1 | 12/2004 | Uchigaki et al. | |
| 2002/0111565 A1 | 8/2002 | Roe et al. | |
| 2003/0018300 A1 | 1/2003 | Duchon et al. | |
| 2003/0028122 A1 | 2/2003 | Marett | |
| 2003/0083685 A1 | 5/2003 | Freeman et al. | |
| 2003/0083686 A1 | 5/2003 | Freeman et al. | |
| 2003/0088191 A1 | 5/2003 | Freeman et al. | |
| 2003/0153900 A1 | 8/2003 | Aceti et al. | |
| 2003/0191376 A1 | 10/2003 | Samuels et al. | |
| 2003/0199789 A1 | 10/2003 | Boecker et al. | |
| 2003/0199790 A1 | 10/2003 | Boecker et al. | |
| 2003/0199893 A1 | 10/2003 | Boecker et al. | |
| 2004/0034318 A1 | 2/2004 | Fritz et al. | |
| 2004/0049220 A1 | 3/2004 | Boecker et al. | |
| 2004/0059366 A1 * | 3/2004 | Sato et al. | 606/182 |
| 2004/0087990 A1 | 5/2004 | Boecker et al. | |
| 2004/0092997 A1 | 5/2004 | Levin et al. | |
| 2004/0096959 A1 | 5/2004 | Stiene et al. | |
| 2004/0122339 A1 * | 6/2004 | Roe | 600/573 |
| 2004/0176732 A1 | 9/2004 | Frazier et al. | |
| 2005/0094680 A1 | 5/2005 | Takabayashi et al. | |
| 2005/0137525 A1 | 6/2005 | Wang et al. | |
| 2005/0143713 A1 | 6/2005 | Delmore et al. | |
| 2006/0200044 A1 | 9/2006 | Freeman et al. | |
| 2006/0264996 A1 | 11/2006 | LeVaughn et al. | |
| 2007/0004990 A1 | 1/2007 | Kistner et al. | |
| 2007/0282362 A1 * | 12/2007 | Berg et al. | 606/181 |

FOREIGN PATENT DOCUMENTS

| | | |
|---|---|---|
| EP | 0014120 | 8/1980 |
| EP | 16198 | 10/1980 |
| EP | 0078724 | 5/1983 |
| EP | 0081975 | 6/1983 |
| EP | 0292928 | 11/1988 |
| EP | 0364621 | 4/1990 |
| EP | 0838195 | 4/1998 |
| EP | 1212138 | 2/2001 |
| EP | 1230895 | 8/2002 |
| EP | 1266608 | 12/2002 |
| EP | 1491143 | 12/2004 |
| EP | 1491144 | 12/2004 |
| JP | 1185245 | 7/1989 |
| WO | 9746157 | 12/1997 |
| WO | 99/55232 | 11/1999 |
| WO | 9955232 | 11/1999 |
| WO | 0003534 | 1/2000 |
| WO | 00/04821 | 2/2000 |
| WO | 01/12330 | 2/2001 |
| WO | 0134030 | 5/2001 |
| WO | 0250534 | 6/2002 |
| WO | 02/056751 | 7/2002 |
| WO | 02/100254 | 12/2002 |
| WO | 02100252 | 12/2002 |
| WO | 02100460 | 12/2002 |
| WO | 02101359 | 12/2002 |
| WO | 03/022330 | 3/2003 |
| WO | 2004039429 | 5/2004 |
| WO | 2004/060163 | 7/2004 |
| WO | 2004060160 | 7/2004 |
| WO | 2004066822 | 8/2004 |
| WO | 2004096959 | 11/2004 |
| WO | 2005000118 | 1/2005 |
| WO | 2005001418 | 1/2005 |
| WO | 2005/049107 | 6/2005 |
| WO | 2005094680 | 10/2005 |
| WO | 2007004990 | 1/2007 |
| WO | 2007005493 | 1/2007 |

* cited by examiner

A

B

METHOD AND APPARATUS FOR SAMPLING AND ANALYSIS OF FLUIDS

CROSS REFERENCE TO PRIOR APPLICATION

This application is a U.S. National Phase of International Patent Application Serial No. PCT/GB2005/003534, filed Sep. 13, 2005, which claims priority from GB Patent Application Serial No. 0420256.0, filed Sep. 13, 2004 the disclosure of both are incorporated herein by reference in their entirety. The International Application was published in English on Mar. 23, 2006 as WO 2006/030201 A1 under PCT Article 21(2).

BACKGROUND TO THE INVENTION

1. Field of the Invention

This invention relates to a sampling and/or dispensing method and apparatus for performing the same. There are many occasions where body fluid samples have to be collected by first piercing the skin and then sampling a fluid, such as blood or interstitial fluid (ISF), or cells contained within. A very important application is the sampling of blood or ISF for various analyses, for example blood glucose, electrolytes or cholesterol. In some applications, for example in the use of Point of Care (POC) instruments, it is important to provide an accurately metered sample of fluid to the instrument. There are also advantages to being able to deposit a fluid (for example antiseptic) on the skin before making an incision.

2. Related art

The most commonly used blood sampling devices are the hypodermic syringe and lancet. Taking a blood sample by either of these methods can be painful for the patient/subject, and can cause distress, particularly in the case of diabetes sufferers who may have to take several blood samples a day. It is for this reason that there has been a trend towards taking smaller quantities of blood and the use of smaller devices penetrating the skin to a lesser depth. Disposable lancets are the commonly preferred devices for puncturing the skin for blood glucose measurement.

Taking a blood sample is only one part of the process. The sample then has to be transferred to a system for analysis. In the case of blood glucose monitoring, a lancet is used to puncture the skin and is then withdrawn. A blood droplet then forms on the surface of the skin and is transferred by capillary or wick to a test strip. This involves the use of several devices in separate steps. Many test devices are used by the subjects themselves rather than by medical staff, so it is important that the whole process is performed accurately with the minimum of user intervention. It is also important to minimise the risk of contamination to the user, and to third parties who could come into contact with sharps contaminated with blood.

In POC testing, the POC instrument is often a bench-top instrument and cannot be taken to the patient, for example, to take a sample of blood from a patient. In such circumstances it is necessary to take a sample of blood or ISF and transfer such to the instrument. It is further desirable that either the sample itself or the dispensed aliquot of the sample be of an accurately measured volume to ensure accuracy of the resulting test.

The prior art in blood sampling describes devices for combining lancing and fluid sampling. U.S. Pat. No. 4,360,016 discloses a capillary channel adjacent and parallel to a lancet. After withdrawing the lancet from the skin, a droplet of blood may fill the capillary by capillary action. WO2004/066822 describes the combination of a lancet and blood glucose test strip with a capillary channel adjacent the tip of the lancet. WO2004/066822 improves upon U.S. Pat. No. 4,360,016 by delivering blood directly to a glucose test strip by capillary action.

WO02/100254 discloses another approach, where a capillary channel is provided with an entrance adjacent a housing containing a lancet, the capillary channel being arranged at an angle to the lancet. A droplet of blood in proximity to the lancet can be drawn by capillary action into the capillary. WO02/056751 describes a lancet within a housing that forms an annular capillary channel concentrically around the lancet between the lancet and the housing. WO2004/060163 also describes a lancet within a capillary tube member such that the clearance between the lancet and housing forms an annular capillary.

Yet another method of capillary sampling is to provide a hollow microneedle in connection with a capillary such that the whole assembly forms a capillary sampling conduit. This may further be integrated with blood glucose sensing. Examples in the prior art include US2004/0096959 and US2003/0153900.

US2004/122339 offers an improvement in fluid flow in capillaries by control of the dimensions and surface energy of the capillary channel. EP1491144 describes a system for sampling ISF. This system includes pressure rings to encourage flow of ISF into the device. The device employs sampling by capillary action.

The present inventors have realised that capillary-based sampling systems work well for many applications, but they do have the disadvantages that there is no control over the timing and rate of sampling once the capillary is presented to the sample; liquid generally will not flow from a narrow diameter capillary to a capillary or sensor chamber of larger diameter; they cannot deliver a fluid to the skin before lancing; most configurations have no provision for ejecting a sample; and they cannot be reversed to eject, deposit or retake a sample.

US2003/0088191 describes a lancet attached to a diaphragm. Air pressure behind the diaphragm is used to drive the lancet tip out of an orifice to pierce the skin. Applying a partial vacuum behind the diaphragm serves to withdraw the lancet and create a negative pressure in a chamber to draw in a fluid sample. The device of US2003/0088191 is intended to sample blood for blood gas analysis in such a way that the sample does not come in contact with air that could contaminate the sample for the intended analysis. It is therefore designed to seal against the skin. The device is provided with two mechanically actuated valves to enable the device to act as a diaphragm pump to suck blood from a wound through a first orifice and deliver it through a second orifice to an external device, such as a blood gas analyser. The device has disadvantages for application to blood sampling for blood glucose determination and POC. The lancet must be fully extended to attempt to eject all the contents, and thus presents a risk of injury.

The device of US2003/0088191 is also not suitable for the procedure of first lancing the subject's skin, allowing a droplet of blood to collect on the skin and then aspirating the droplet of blood. (As will be seen, this is one aspect of the present invention, set out in detail later.) This is because the lancet has to be extended to permit aspiration without admitting a significant volume of air. The device is also not particularly suited to delivering a small sample of blood back out through the original sampling orifice. Depending on the orientation of the device, air within the chamber may push past the blood and exit instead of or before the blood sample when the device is reversed to dispense the sample. The use of a diaphragm driven by air and the compressibility of the air headspace can make it very difficult to exert close control over the sampling and dispensing volumes. The device of US2003/0088191 is therefore most suited to its intended application of aspirating an approximate volume of blood in the absence of air and transferring part of that volume to another external blood gas analyser. The transferred volume is unlikely to be of high precision.

U.S. Pat. No. 5,569,287 discloses a blood sampling device utilising a trigger mechanism to push a needle into a puncture position by operation of a piston. Sampling of a blood drop is achieved by withdrawing the piston along its barrel, creating a partial vacuum in a headspace above the blood drop, drawing a blood sample into tube surrounding the needle. The separation of the piston and sample has the disadvantage that it is difficult or impossible accurately to meter the volume of blood drawn into the device. Additionally, the trigger mechanism ensures that forward displacement (at least) of the needle does not occur in fixed relation to movement of the piston.

Another group of prior art devices are the devices that employ suction to draw blood to the surface of an incision. The purpose of these is to help to draw blood to the surface at "alternative testing sites", such as the arms or legs, that are less painful than the fingers, but are more difficult to draw blood from. U.S. Pat. No. 4,653,513 describes a system having a lancet attached to a plunger. The plunger is provided with a piston seal and moves within a parallel bore. The forward end of the bore is provided with a gasket to seal onto the skin of the user when pressed firmly in contact. The lancet and plunger are driven down together to pierce the skin and then fully retracted under spring force to create a partial vacuum in the bore. The purpose of this device is to apply suction around the lanced incision to create a droplet of blood on the surface of the skin. The blood droplet remains on the skin and is sampled by another device when the suction device has been removed. The device of U.S. Pat. No. 4,653,513 cannot aspirate or contain a blood sample and has no provision for doing so.

U.S. Pat. No. 5,368,047 describes an improvement over U.S. Pat. No. 4,653,513 containing a separate lancet and plunger. The inventor describes a disadvantage of U.S. Pat. No. 4,653,513, where the friction of the piston seal in the device is detrimental to the lancing action. U.S. Pat. No. 5,369,047 solves this problem by providing a low friction lancet that does not seal at any point in the bore, and a separate syringe assembly at the other end of the device to create a vacuum. Three integral springs are used to drive the device. Once again, the device is designed to cause a sessile drop of blood to form on the surface of the skin for another system to sample from, and has no provision for aspiration or containment of the blood sample within the lancing device described. Further examples of this type of device are provided in U.S. Pat. No. 2002/111565 and WO9955232. The figures contained in WO9955232 are particularly useful in demonstrating how suction devices encourage a droplet of blood to be drawn to the skin surface by applying vacuum to the wound site and thereby allow for subsequent sampling by another device.

The present inventors have realised that it may be desirable in some cases to be able to deliver a fluid to the site of the incision before the incision is made. Such fluid may be for example an antiseptic to prevent infection or an anaesthetic to reduce the pain of incision. This would be a useful function for a blood sampling system. It may also be desirable that a fluid be delivered to the skin that has a diagnostic function, for example the use of allergens to diagnose allergies.

It is now common practice in doctors surgeries or allergy clinics to test patients complaining of allergic reactions such as urticarial rashes for sensitivity to common allergens such as house dust, moulds, dairy products, etc, by dispensing a drop of liquid containing one such allergen to the skin surface and lancing the skin through the dispensed drop of liquid. It is not necessary to lance the skin deeply for this test, as the intent is to damage the skin and provoke a histamine-mediated inflammation reaction, rather than produce a sample of blood at the puncture site.

If an allergic reaction occurs to the allergen present at the puncture site, this is evidenced by a histamine-induced localised swelling of the skin at the puncture site that creates a defined circular patch of raised, inflamed skin within 10 minutes of the puncture. The size of the weal or swelling produced at the puncture site after 10 minutes is an indication of the severity of the allergic reaction. In current practice for skin-prick allergy tests, a negative control is normally provided by substituting distilled water for allergen solution, where no appreciable swelling would be expected. A positive control is normally provided by substituting dilute histamine solution for allergen solution. This should result in significant swelling at the puncture site.

It is common practice in allergy testing to make an array of such punctures on the skin of the forearm as quickly as possible so that the time between the first and last puncture of the series is a short as possible, and also to label or mark the skin adjacent to each puncture site to record which allergen was used at which puncture site.

Commercial lancet devices are available to delivering allergens to the skin before piercing the skin. Examples include the Quintip™ from Hollister Steer Laboratories LLP, and the GreerPick™ from Greer Laboratories. These devices employ surface tension passively to pick up an allergen solution from an open reservoir for transfer to the skin and an integral lancet to pierce the skin.

The prior art discloses several arrangements involving the use of microneedles to deliver fluids beneath the skin by a minimally invasive method. Examples of microneedle devices and arrays for fluid delivery can be found in US2005/143713, US2005/137525, WO2005/049107, WO2003/022330 and CN1562402. Such microneedle systems are designed to deliver a fluid beneath the skin through an incision, not to deliver a fluid to the skin before incision. Microneedles are generally more invasive than lancets because the needle has to be of sufficient diameter to be hollow.

The present inventors therefore consider that it is thus desirable to be able to perform any or a combination of some or all of the actions of fluid delivery, piercing, sample collection, sample transfer and analysis using a single device. The damage to tissue and the pain experienced by the subject is also known to be related to the diameter of the lancet or hypodermic needle. It is therefore also desirable that the cross-sectional area of the skin piercing component of the sampling device is minimised.

Efficient liquid sampling and depositing systems in the form of laboratory pipetting systems are known. U.S. Pat. No. 5,413,006 and EP0364621 represent typical examples of air-displacement pipettors with separate pipette tips. EP0078724 describes a hand-held positive displacement pipettor with disposable tips. EP1212138 describes a miniaturised positive-displacement pipette capable of aspirating and dispensing sub-microliter volumes of liquid, while WO0112330 describes how such pipettes may be attached to a continuous strip for automated pipetting. These devices can aspirate and dispense fluids to high accuracy, but have no capability to pierce the skin or to affect an analysis.

SUMMARY OF THE INVENTION

It is an object of the present invention to address, avoid or even overcome one or more of the problems identified above. For the avoidance of doubt, the problems set out above are not themselves part of the prior art, but the discussion of those problems identified by the present inventors is included in that section of this specification to assist the reader in understanding the present invention.

In a first aspect, the present invention provides a medical device having a housing with a bore and a lancet slidably fitting in the bore, the lancet being moveable between a puncture position, in which a sharpened tip of the lancet is exposed from a forward end of the bore for a puncture operation, and a retracted position, in which the lancet is rearwardly displaced along the bore to define a fluid-containing space in the bore forwardly of the lancet tip, the fluid-containing space having a cross-section dimension to allow fluid to be retained therein by surface tension, the device having seal means operable substantially to prevent flow of fluid from the fluid-containing space past the seal means on movement of the lancet, so that displacement of the lancet between the puncture and retracted positions provides at least one of:
  (i) suction for drawing fluid into and along the fluid-containing space from the forward end of the bore, and
  (ii) pressure for expelling fluid from the fluid-containing space via the forward end of the bore.

In this way, the present invention allows the taking and/or transferring of blood, ISF or other samples that exist in a fluid or semi-fluid state (e.g. tissue samples such as biopsies) and/or depositing a fluid to the skin.

Preferably, the lancet acts as a piston within the bore, so that fluid can be moved within the device by positive displacement. The seal may be a piston seal or a rod seal or may be an interference fit.

In use, the lancet (or "lancet piston") is projected beyond the end of the bore to penetrate the skin to cause a wound and is then withdrawn. After waiting for blood or ISF or other fluid to evolve from the wound, a blood or ISF or other sample can then be drawn into the bore by retraction of the lancet piston where it may be metered and held for subsequent ejection into another device or compartment, or may be transferred to sensors or a chamber for analysis within the bore itself or connecting channels. The device may also deliver fluids by positive displacement to the skin before lancing. The device may be driven manually, by spring, hydraulic, pneumatic, electrical force, or with the aid of a motorised, automated system.

The invention provides for a smaller cross-sectional area for the penetrating component than an equivalent hypodermic syringe needle of the same bore for the sampling conduit. For example, a hypodermic syringe microneedle with a bore of 300 μm diameter would have an outside diameter of perhaps 500 μm. With the present invention, the lancet piston would be the same outside diameter (300 μm) as the inside diameter of the sampling conduit.

The invention offers an instant improvement over the use of capillaries for sampling fluids because, by using positive displacement, it may achieve a theoretical head of 10 m of water for all suitable bore diameters compared with a head of only tens of centimeters for practical capillaries of 50 μm diameter and above. Some embodiments of the invention are also able to maintain sample flow when the fluid encounters an increase in the diameter of the sampling channel (for example a chamber, step or taper) where capillary flow would otherwise stop.

The use of the positive displacement principle also allows samples of viscous fluids, including those with high solids content, to be aspirated and dispensed without causing separation of the solids content from the bulk fluid. Particulates in a sample are far less likely to block the bore of the device when compared with capillary devices. High solids content fluids include blood with high cell content, partially clotted blood and cell suspensions.

The device may in particular be disposable, as is normally required for "sharps" used to pierce the skin.

In a second aspect, the present invention provides a method of operating a medical device, the device having a housing with a bore and a lancet slidably fitting in the bore, the lancet being moveable between a puncture position, in which a sharpened tip of the lancet is exposed from a forward end of the bore for a puncture operation, and a retracted position, in which the lancet is rearwardly displaced along the bore to define a fluid-containing space in the bore forwardly of the lancet tip, the fluid-containing space having a cross-section dimension to allow fluid to be retained therein by surface tension, the device having seal means operable substantially to prevent flow of fluid from the fluid-containing space past the seal means on movement of the lancet, the method including displacing the lancet between the puncture and retracted positions to do least one of:
  (i) drawing fluid into and along the fluid-containing space from the forward end of the bore by suction, and
  (ii) expelling fluid from the fluid-containing space via the forward end of the bore.

In a third aspect, the present invention provides a device according to the first aspect, for use in a method of treatment of the human or animal body by surgery or therapy or in a diagnostic method practised on the human or animal body.

In a fourth aspect, the present invention provides a device according to the first aspect, for use in allergy testing of the human or animal body.

In a fifth aspect, the present invention provides a device according to the first aspect, for use in sampling blood or interstitial fluid from the human or animal body for subsequent diagnostic testing.

In a sixth aspect, the present invention provides a use of the device according to the first aspect in carrying out a diagnostic test on the sampled fluid.

Preferably, the step of obtaining the sample is excluded from the sixth aspect, the sampled fluid being ex vivo.

In a seventh aspect, the present invention provides a use of a single use device according to the first aspect in the manufacture of a medical device for allergy testing of the human or animal body.

In an eighth aspect, the present invention provides a use of a single use device according to the first aspect in the manufacture of a medical device for diagnostic testing of the human or animal body.

Preferred and/or optional features of the invention will now be set out. These are applicable either singly or in any combination with any aspect of the invention, unless the context demands otherwise.

Preferably, the fluid is one of a liquid, a mixture of liquids and a mixture of liquid or liquids with solid or solids.

Preferably, the seal means is in slidable engagement with a sealing surface, one of the seal means and the sealing surface being movable (preferably fixedly movable) with the lancet, at least during forward displacement of the lancet. Said one of the seal means and the sealing surface may be fixedly movable with the lancet during rearward displacement of the lancet.

The seal means may be formed by the outer surface of the lancet, the sealing surface being an internal surface of the bore. The outer surface of the lancet may be profiled to provide the seal means as a surrounding projection. For example, the outer surface of the lancet may provide an annular projection. Alternatively, the seal means may be a sealing member disposed around the lancet, the sealing surface being an internal surface of the bore. In these embodiments, the seal means may still move with the lancet.

In alternative embodiments, the seal means is a sealing member disposed at the internal surface of the bore, the sealing surface being an outer surface of the lancet. Here, the seal means will not usually move with the lancet.

Preferably, the seal means is disposed adjacent the lancet tip, at least when the lancet is in the retracted position. The advantage of this is that it is then possible to avoid a large head space of compressible fluid above the (normally substantially incompressible fluid sample), thereby improving metering accuracy. The seal means may be located within a distance of 20, 10 or 5 bore diameters from the lancet tip, preferably within a distance of 2.5 or one bore diameters or less.

In some embodiments, the lancet tip may be disposed forwardly of the seal means, when the lancet is in the retracted position. In such cases, the lancet may be formed from a spike member protruding from a support, the support sealing against the internal surface of the bore. In these embodiments, the lancet tip itself may protrude into the fluid-containing space.

Preferably, the device has cooperating means for providing an intermediate delay position for the lancet between the puncture position and the retracted position. The intermediate delay position acts to halt the retraction of the lancet tip after puncturing the skin. This delay allows fluid to accumulate on the skin before drawing it into the fluid containing space by further retraction of the lancet.

Preferably, the device has at least one stop member for limiting the forward and/or rearward travel of the lancet.

At the puncture position, the seal means may be out of contact with the sealing surface, or may contact the sealing surface with reduced pressure compared with the retracted position, thereby providing low friction for movement of the lancet at the puncture position. During retraction from the puncture position, the contacting or increased contacting of the seal means with the sealing surface may provide the intermediate delay position set out above.

Preferably, the bore includes a region of increased cross-section dimension for location of the seal means or the sealing surface at the puncture position of the lancet. The seal means or sealing surface may be disposed beyond the forward end of the bore at the puncture position of the lancet.

Preferably, the seal means is a sealing member (e.g. a piston seal) disposed rearwardly in the device from the forward tip of the lancet and movable with the lancet tip and the sealing surface is formed by the internal surface of a sealing region of the bore. Typically, a characteristic cross-sectional dimension (e.g. diameter) of the sealing member is greater than a cross-sectional dimension of the fluid-containing space but less than or equal to 10 (preferably 5, more preferably 2) times the cross-sectional dimension of the fluid-containing space.

Preferably, the lancet tip is sharpened to have a radius of curvature in at least one dimension of one quarter or less of the narrowest cross-sectional dimension of a non-tip region of the lancet. This radius of curvature is more preferably one sixth or less, one eighth or less, or most preferably one tenth or less of the narrowest cross-sectional dimension of a non-tip region of the lancet.

Preferably the bore has an internal cross sectional dimension of 5 mm or less. This is a suitable internal diameter to allow a suitable quantity of blood, for example, to be retained in the fluid-containing space by surface tension against gravity. The bore may be narrower than 5 mm, for example 4 mm or less, 3 mm or less, 2 mm or less, or 1 mm or less.

The lancet will be sized to fit within the bore via the seal means. The cross-sectional dimension of the lancet (typically a non-tip region of the lancet) is preferably 0.1 mm or greater. More preferred ranges for this dimension are 0.2 mm or greater, 0.3 mm or greater, 0.5 mm or greater, or 0.8 mm or greater. Alternatively, the cross-sectional dimension of the lancet (typically a non-tip region of the lancet) may fall within the ranges specified above for the bore dimensions.

The volume of the fluid-containing space when the lancet is in the retracted position may be 0.1 microliters or more. Preferably this volume is 0.2 microliters or more, 0.5 microliters or more, 1 microliter or more, 5 microliters or more or 10 microliters or more. This volume is typically 300 microliters or less. Preferably this volume is 250 microliters or less, 200 microliters or less, or 150 microliters or less.

Preferably, the bore includes a chamber portion, disposed between and having a greater cross-sectional dimension than forward and rearward portions of the bore. The cross-sectional dimension of the bore may increase stepwise between the forward portion of the bore and the chamber portion.

In use, the fluid-containing space may present means for measuring or testing a characteristic of the fluid contained in the fluid-containing space, e.g. at the chamber portion.

The optional incorporation of a sensor chamber offers a means to integrate test-strip chemistry to perform electrochemical or immunological tests. Sensors may also be incorporated to enable physical measurements of blood properties to be made. Examples of the type of tests that may be integrated with the device include blood glucose concentration, HbA1c (glycated haemoglobin), cholesterol, triglycerides, blood ketone, cardiac markers, (e.g. troponin I, myoglobin, D-dimer, CK-MB, BNP), osteoporosis tests ions and electrolytes (e.g. pH, Na+, K+, Ca++, Cl—) and prothrombin time (PT). It will be understood that the invention is not necessarily limited to the use of these examples and can be applied to many methods of blood analysis performed in small chambers.

Preferably, the device has a secondary conduit from the bore, communicating with the fluid-containing space. This allows connection, for example, of the bore with a reagent reservoir, e.g. in the form of a bladder. Alternatively, the secondary conduit may provide an alternate outlet for the sample contained in the fluid-containing space.

The device may have a closure member located forwardly of the lancet tip, for sealing at least a part of the fluid-containing space. The closure member may be adapted to be removed or punctured by the lancet during operation of the device. The fluid-containing space may contain a liquid for application to a subject by operation of the device. For example, the liquid may be an allergen testing liquid, anaesthetic liquid, anticoagulant liquid or an antiseptic liquid.

Preferably, the device includes a spacer member located forwardly of the forward end of the bore, the spacer member being for contact with the skin of a subject. The spacer member may be dimensioned to provide an accumulation space between a puncture in the skin of the subject and the forward end of the bore, fluid from the puncture being able to accumulate in the accumulation space before being drawn into the fluid-containing space by operation of the device. Preferably the spacer member has a transverse dimension of 5 mm or less. The axial extent of the spacer member may be 10 mm or less. The forward end of the bore may be located within the space enclosed by the spacer member. The fluid drop accumulating on the skin surface within the accumulation space need not contact any part of the spacer member. However, in some embodiments, such contact may be suitable to encourage flow of said fluid towards the forward end of the bore. The spacer member may include one or more projections projecting inwardly towards the puncture position of the lancet tip. These projections may provide a surface to enhance the flow of an accumulating fluid towards the forward end of the bore.

The device may include sensing means for sensing the presence or absence of fluid at the forward end of the bore. The sensing means may include at least two electrodes, at least one of which is located at the forward end of the bore to detect the presence or absence of fluid at the forward end of the bore by measurement of the resistance between the electrodes. For example, the lancet may provide one of the electrodes.

The device may include sensing means for sensing the presence and/or amount of fluid along the fluid-containing space. Preferably, the sensing means includes at least two electrodes, one of which may be the lancet tip. The other electrode may be towards the rearward end of the bore. With this arrangement, when the fluid-containing space is filled with fluid having some conductivity but a high resistance (e.g. blood), there will be a high resistance (but not an open circuit) between the electrodes when the lancet tip is retracted, since the fluid should still be in contact with the lancet tip. Knowledge of the position of the lancet (by observation) with respect to the bore will provide an indication of the volume of fluid in the bore since the fluid is in contact with the lancet tip and the bore dimensions are known. The presence or entrainment of any significant air bubble in the fluid-containing space will be indicated by a high resistance or by a jump in resistance.

Preferably, in use of the device, the puncture operation of the lancet tip punctures the skin of a subject and the fluid drawn into the fluid-containing space is at least one of the blood of the subject and the interstitial fluid of the subject. Preferably, the mode of operation of the device includes the step, after puncturing the skin of the subject, of delaying retraction of the lancet at an intermediate delay position to allow blood or interstitial fluid to accumulate on the surface of the skin of the subject for subsequent drawing into and along the fluid-containing space.

In a preferred use of the device, there is included the step, before puncturing the skin of a subject, of expelling fluid from the fluid-containing space onto the skin of the subject at the skin location to be punctured. This provides the advantage that the fluid is applied to the skin before the puncture operation, which is of use particularly in allergy-testing applications.

In preferred uses, the device can eliminate the need to use separate devices for piercing the skin, sampling and metering the blood or fluid. Preferred embodiments of the device allow transfer of the fluid sample to a sensor or analysis chamber. Further embodiments are capable of delivering a fluid to the skin before piercing. The device may be operated under automated control.

BRIEF DESCRIPTION OF THE DRAWINGS

Examples of the invention will now be described by way of example with reference to the accompanying drawings, in which.

DETAILED DESCRIPTION OF PREFERRED EMBODIMENTS

Figure 1:
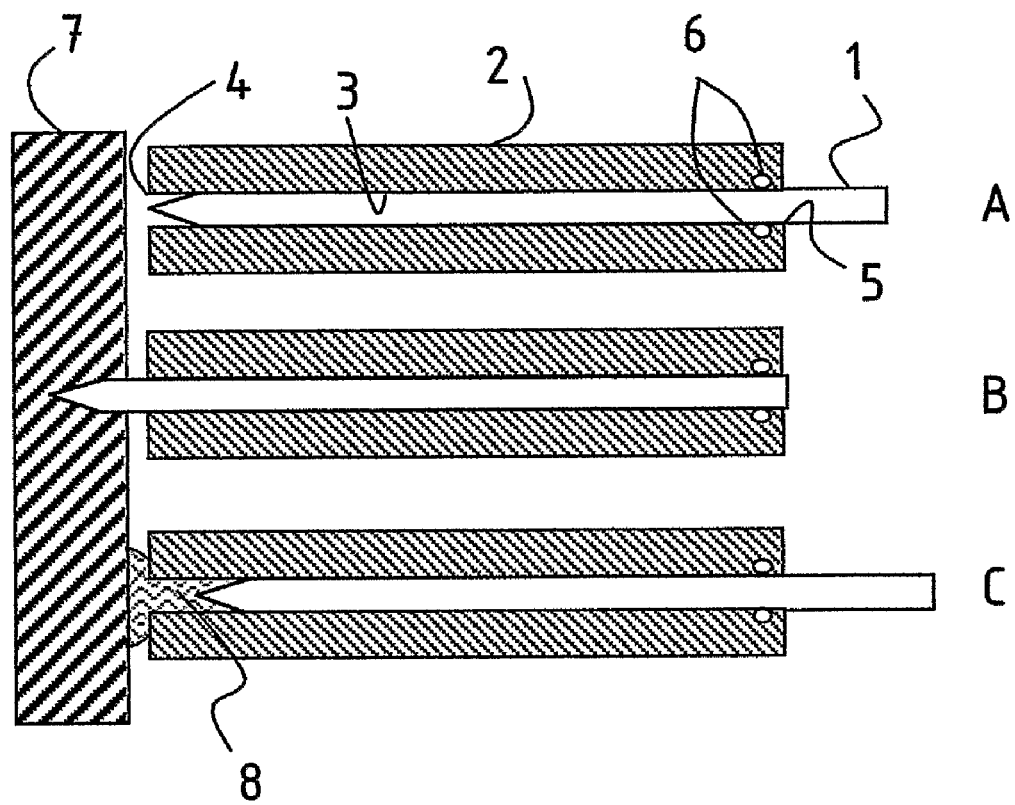
FIG. 1 is a schematic cross-sectional view of a device according to an embodiment of the present invention, illustrating the principle of piercing and sample transport.

Use of the devices according to the preferred embodiments of the invention may provide a suitable method for piercing tissue, sampling and/or dispensing fluid, and optionally performing processing or analysis on the fluid. In the device, a lancet is housed within a bore wherein the lancet conforms to the bore over at least part of the length of the bore or a seal is provided between part of the lancet and bore such that part of the lancet forms a piston against the bore walls. Movement of the lancet piston with respect to the bore can draw fluid into the bore or eject it therefrom. The device may further incorporate chambers, fluid connections or sensors. In use, the tip of the lancet piston is extended beyond the end of the bore to plunge the tip of the lancet piston into the skin or tissue to pierce it. The lancet piston tip is then withdrawn into the bore. If necessary, the rearward movement of the lancet piston is paused to allow fluid to accumulate if necessary. Then, the lancet piston is further withdrawn into the bore such that fluid is drawn into the bore.

The movement of the lancet piston within the bore may be employed to move fluid to connecting channels, chambers or sensors or to eject fluid to other receptacles or systems.

The piercing step may alternatively be carried out by retaining the lancet piston tip within the bore, presenting the end of the bore to the skin or tissue, driving the tip of the lancet piston beyond the end of the bore to pierce the skin or tissue, and then withdrawing the lancet piston back into the bore.

The present invention may further comprise the step of determining the depth of the sample fluid (into which the sampling end of the device is immersed) by means of electrodes integrated with the device.

Optionally, prior to lancing of the skin, the bore ahead of the lancet piston may contain fluid when the lancet piston is partially or fully retracted so that such fluid is delivered to the skin when the lancet piston is driven out to pierce the skin.

The present invention also provides an apparatus for piercing, taking a fluid sample, and manipulating and/or analysing said sample. The apparatus comprises a lancet housed within a bore wherein the lancet conforms to the bore over at least part of the length of the bore or a seal is provided between part or all of the lancet and bore such that the lancet forms a piston within the bore over at least part of its travel and movement of the lancet with respect to the bore can draw fluid into the bore or eject it therefrom, the piercing end of the lancet piston being capable of being extended beyond the end of the bore and any nozzle. The nozzle is provided at the forward (or open) end of the bore of inside diameter (ID) in the range 0.1 to 5 mm, preferably 0.2 to 3 mm ID. There is also provided a means of moving the lancet piston with respect to the bore, and a means of controlling the movement of the lancet piston.

The bore is contained within a device that may further incorporate chambers, fluid connections or sensors. The apparatus may further incorporate electrodes, at least one being attached to or forming part or all of the lancet piston, and with at least one further electrode attached to or forming part of the device containing the lancet piston such that the presence of a conducting fluid (for example, but not limited to, blood) may be detected when said fluid comes into contact with two or more electrodes.

These electrodes may be arranged such that they can be used to determine that the fluid into which the device is partially immersed is of sufficient depth or volume to be a viable sample for analysis, and furthermore, by maintaining electrical connection across the fluid it is possible to establish if the fluid is filling the bore as the lancet piston is being drawn up within it.

The lancet piston may preferably be made of metal, plastic, or ceramic or may be an assembly of a piston made of plastic or other suitable material tipped with a lancet point (or spike) made of metal, ceramic, hard plastic or any other suitable hard material. A lancet piston made up of several components of the same or different materials shall still be regarded as a single lancet piston, in the same way that a lancet of the prior art is commonly constructed of a metal wire fashioned to a point and fused to a plastic support. The lancet piston may also incorporate an elastomeric sealing member to seal onto the bore. The component in which the bore is formed may be fabricated in preferably plastic or a synthetic resin and may be a single part or a fabrication of several parts, for example several layers.

The lancet piston may preferably be of circular cross section, but is not limited to this. The lancet piston may be of a single diameter or thickness along its length or may incorporate one or more variations in diameter or thickness along its length. Such increases in diameter or thickness may serve as different diameter pistons or as a dead stop feature to limit travel of the lancet piston and hence limit depth of penetration of the skin by the lancet, or to define a fixed volume of sample. The piercing tip of the lancet piston is preferably conical or of another profile that ensures the sharp point does not contact the bore to avoid damage to the bore when driving it out of the bore to eject fluid, but can alternatively be of any profile that is suitable for piercing skin.

Lancet points are generally described in sizes related to the gauge of the wire stock from which the piercing point of the lancet is formed. For example, a 25-gauge lancet is formed from a wire of 25 gauge (0.455 mm OD) with the tip ground to a point over a region of a few millimeters. The penetrating region of the lancet piston of the present invention may be formed from a base stock with a diameter or minimum thickness within the range 0.1 mm to 1 mm and preferably within the range 0.2 mm to 0.8 mm, the tip being fashioned to a sharp point. The term "minimum thickness" refers to the minimum thickness across the lancet piston if this is of non-circular cross-section. The lancet piston and corresponding bore may have a diameter or other characteristic minimum cross-sectional dimension within the range 0.1 mm to 5 mm, preferably within the range 0.2 mm to 4 mm and may have one or more sections of different diameter or cross-section within these ranges along its length. The bore and stroke of the lancet piston and housing may be chosen to accommodate a fluid sample in the range 0.1 microliters to 300 microliters, preferably 0.2 microliters to 150 microliters, when the lancet piston is fully retracted.

The lancet piston may be provided with a feature or features to enable the lancet piston to be gripped or driven by an integrated or external actuator. This feature may include a fixed or adjustable dead stop to limit the travel of the lancet piston.

The movement of the lancet piston within the bore may be performed and controlled by manual operation, spring force, pneumatic force, hydraulic force, electrical force motorised operation under automatic control or a combination of the above.

FIG. 1 shows a cross-section through an example device in three configurations, A, B and C. A lancet piston 1 is enclosed within a bore 3 in a housing 2 such that the lancet piston is able to freely move in the direction of its long axis and the inner walls of the housing form a bore 3. The lancet piston is sealed onto the bore by means of a rod seal 6 or interference fit or piston seal (not shown). In configuration A the lancet piston is held within the bore so that the point is protected inside the forward end 4 of the bore 3. In configuration B the lancet piston protrudes from the forward end of the bore to puncture the skin 7. In configuration C a droplet of blood or other fluid 8 has formed and some of this fluid is drawn within the bore by the action of withdrawing the lancet piston into the bore. The movement of the lancet piston may be reversed to eject the sample. If the piston seal is near the tip end of the lancet piston, it is possible to arrange that no air (or substantially no air) will be present between the piston seal and the sample fluid. If a rod seal is used or the piston seal is positioned on the lancet piston some distance from the tip of the lancet piston then air (or other fluid) may be present in the void between the piston or rod seal and the sample. However, in practice the clearance between the bore 3 and the lancet piston 1 is chosen to be as small as possible (in effect, a sliding interference fit), with no or negligible air space being present. The purpose of the rod seal is primarily to prevent air from being drawn into the bore from the rearward end 5 of the bore 3, or to prevent fluid leaking out of the rearward end 5 of the bore 3 when the lancet piston is ejecting the liquid contents of the bore. In use, fluid acts to seal the very small gap between the bore and piston if such a gap exists.

FIG. 1 illustrates a bore without a restricted nozzle at the forward (or open) end of the bore. If the bore has an ID of less than 5 mm, preferably 0.2 to 3 mm, the surface tension of aqueous liquid (such as blood) will assist in retaining the liquid within the bore and avoid the liquid from dripping out of the forward end when the end of bore it is taken out of a liquid sample. A small diameter aperture to the forward end of the bore is equally important to ensure that air is not drawn past the fluid into the device when aspirating a sample. It is further important to have a relatively small bore ID aperture to the forward end of the bore to enable the end of the bore to be immersed in a droplet of blood on the skin, said droplet being typically of the order of only a few millimeters across. A small aperture is also important where a liquid sample is to be ejected to a small area (for example, a test strip, or small region of the skin). Apertures in the range of 0.2 to 3 mm ID for the end of the bore are preferred because in practise an aperture of up to 3 mm ID is effective at retaining fluids through surface tension and localising delivered droplets (the smaller the aperture, the better), and the aperture has to be of larger ID than the OD of the piercing end of the lancet piston that has to pass through the aperture. A practical lower limit for the shaft of a lancet to pierce skin is likely to be 0.1 mm OD or above. It should be noted that fluid drawn into the bore as shown in FIG. 1 step C will be held in place in the bore both by surface tension and by the fact that the rearward end of the bore is sealed by the lancet piston. This sealed rearward end of the bore would create a vacuum in the bore forward of the seal to oppose the tendency for dripping of the aspirated sample from the forward end of the bore under the influence of gravity.

FIG. 1 illustrates the operation of the invention with the apparatus held a short distance off the skin with only the lancet piston coming in contact with the skin. The apparatus of the invention may alternatively be held against the skin, or may incorporate a feature that contacts the skin but holds the forward end 4 of the bore 3 off the skin. The piercing operation may alternatively be performed by holding the assembly away from the skin, driving the tip of the lancet piston out beyond the end of the bore (the lancet piston may already be assembled in this position) and then driving forward both the lancet piston and bore together as one unit such that the protruding tip of the lancet piston punctures the skin. There are several options for withdrawing the lancet piston and taking the fluid sample, examples being:

a) The lancet piston alone may then be retracted, leaving the bore in contact with the skin. The fluid is withdrawn into the bore by further withdrawing the lancet piston into the bore;

b) The lancet piston and bore may be withdrawn from the skin together such that the lancet piston remains protruding from the bore. The lancet piston is then retracted such that the tip of the lancet piston point is aligned with the forward end of the bore. Once a droplet of fluid has formed the bore may be brought into contact with the fluid and the lancet piston may be withdrawn further into the bore, drawing fluid into the bore;

c) The lancet piston and bore may be withdrawn from the skin together such that the lancet piston remains protruding from the bore. A drop of fluid may then be allowed to form around the protruding lancet piston. The lancet piston and bore may be further retracted, leaving a droplet of fluid on the point of the lancet piston. This fluid may then be drawn into the bore by further retraction of the lancet piston;

d) The lancet piston alone may be retracted, leaving the bore in contact with the skin. The lancet piston and bore together may then be moved off the skin to a position close enough for a droplet of fluid to bridge the gap as shown in FIG. 1 configuration C. The fluid is withdrawn into the bore by further withdrawing the lancet piston into the bore;

or any combination of these actions.

Figure 2:
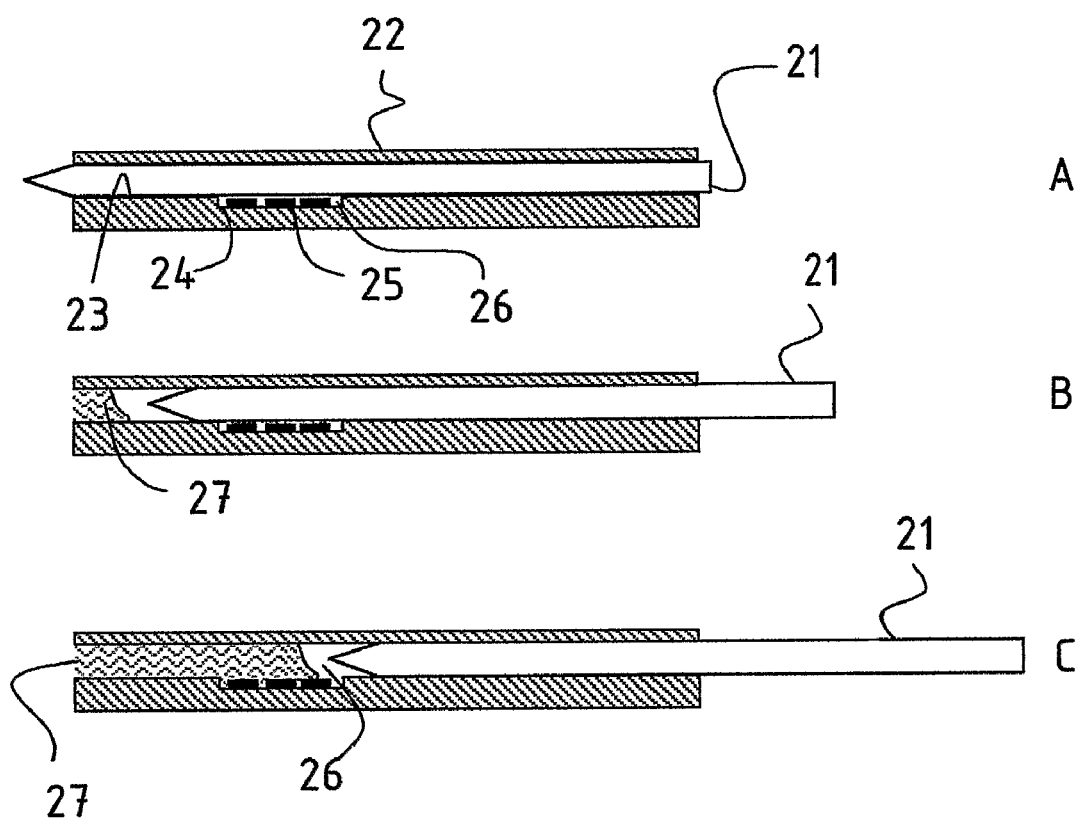
FIG. 2 is a schematic cross-sectional view of a device according to an embodiment of the present invention, illustrating the transport of a fluid sample to an analysis chamber and sensors.

The apparatus of embodiments of the invention may also incorporate one or more chambers for analysis of fluid samples and may contain sensors therein. FIG. 2 illustrates several configurations (A, B and C) for one embodiment where the housing 22 incorporates a chamber 24 with an opening to the bore 23. This chamber may contain sensors 25, for example for the determination of blood glucose concentration. Configuration A shows the lancet piston 21 before drawing in fluid. In configuration B the lancet piston 21 draws fluid 27 into the bore 23 as it is retracted. In configuration C the lancet piston 21 has passed beyond the chamber 24 and draws air 26 out of the chamber, pulling fluid 27 into the chamber. Careful attention to the design of the chamber and the wetting properties of surfaces can result in the air and fluid not mixing. This operation illustrates that the apparatus of the invention can transport liquid across regions of increased cross-section within the bore and associated chambers. This is not usually possible with capillary transport of liquids as currently used in blood glucose and other sensing devices.

Figure 3:
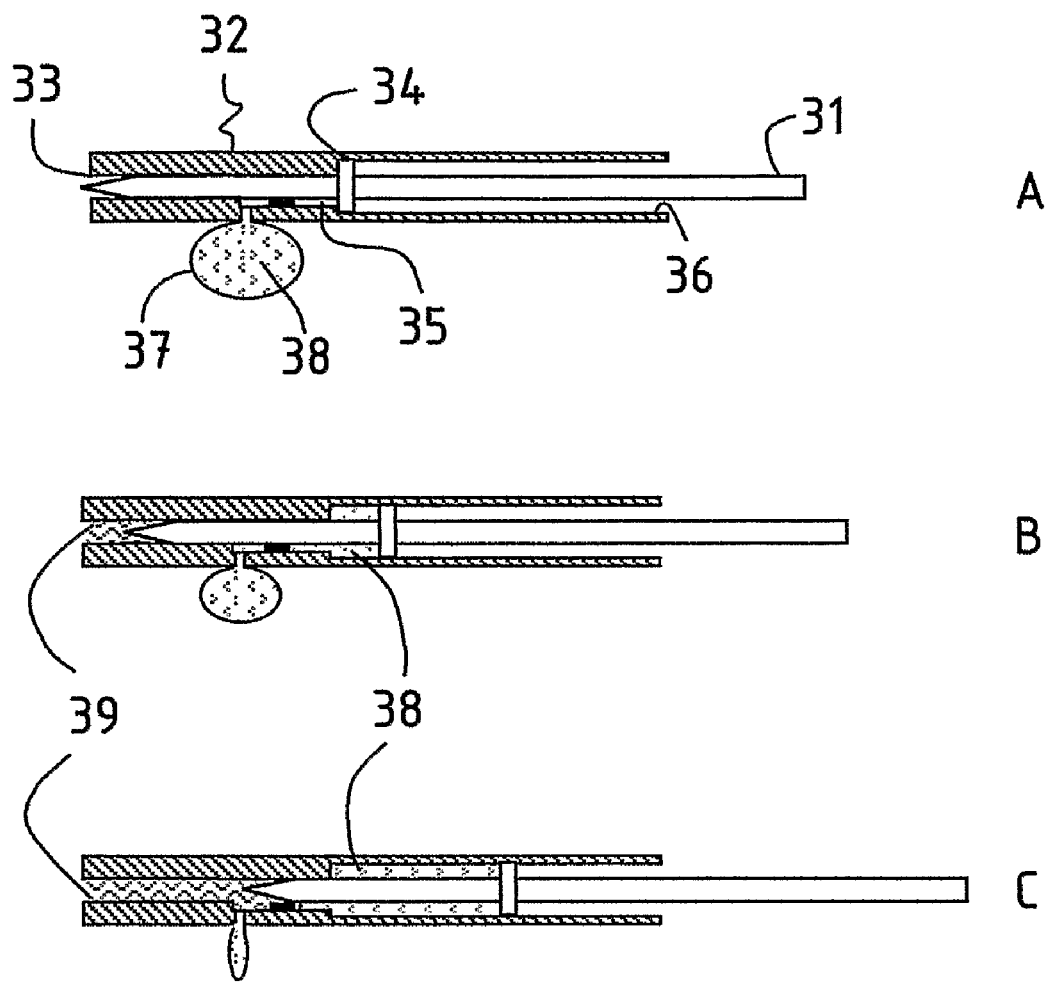
FIG. 3 is a schematic cross-sectional view of a device according to an embodiment of the present invention having a stepped lancet piston, the same being employed to transport a second fluid sample to an analysis chamber in addition to a first sample.

The lancet piston may also incorporate different diameter sections as shown in FIG. 3 (again showing three configurations A, B and C). The lancet piston 31 has a thicker section or collar 34 attached to it, this forming a piston seal. The bore 33 has a corresponding region of increased cross-section 36 in which the collar 34 can slide and seal. In this example a bladder 37 (alternatively, a vented chamber) is filled with a liquid reagent 38. Configuration A shows the lancet piston 31 before drawing in fluid. At configuration B the lancet piston 31 has been drawn back to suck in fluid 39 at the forward end of the bore and reagent 38 from the bladder 37 forward of the collar 34. This causes the reagent 38 to flow through the chamber 35. If the lancet piston is further withdrawn to configuration C the reagent 38 is fully used up and the sample fluid 39 is now drawn through the chamber 35. Such sequential delivery of reagent and sample can be useful, for example to wash or hydrate sensors before the sample is presented to them, or to introduce a reagent for a chemical or biochemical assay such as a blood-glucose concentration determination or a sandwich immunoassay.

By using a piston instead of a capillary the invention allows close control over the rate of sampling and the timing of fluid transport. For example, collection of the sample can be suspended until it is determined that there is sufficient sample for whatever operation is intended. The device may remain in contact with the sample and then proceed to take a sample at the appropriate time. The fluid sample may also be stopped within the bore at any point (including at a sensing chamber), and can be arranged to flow through sections of the device at any desired rate within the range of stroke speed achievable by the lancet piston driving system.

Figure 4:
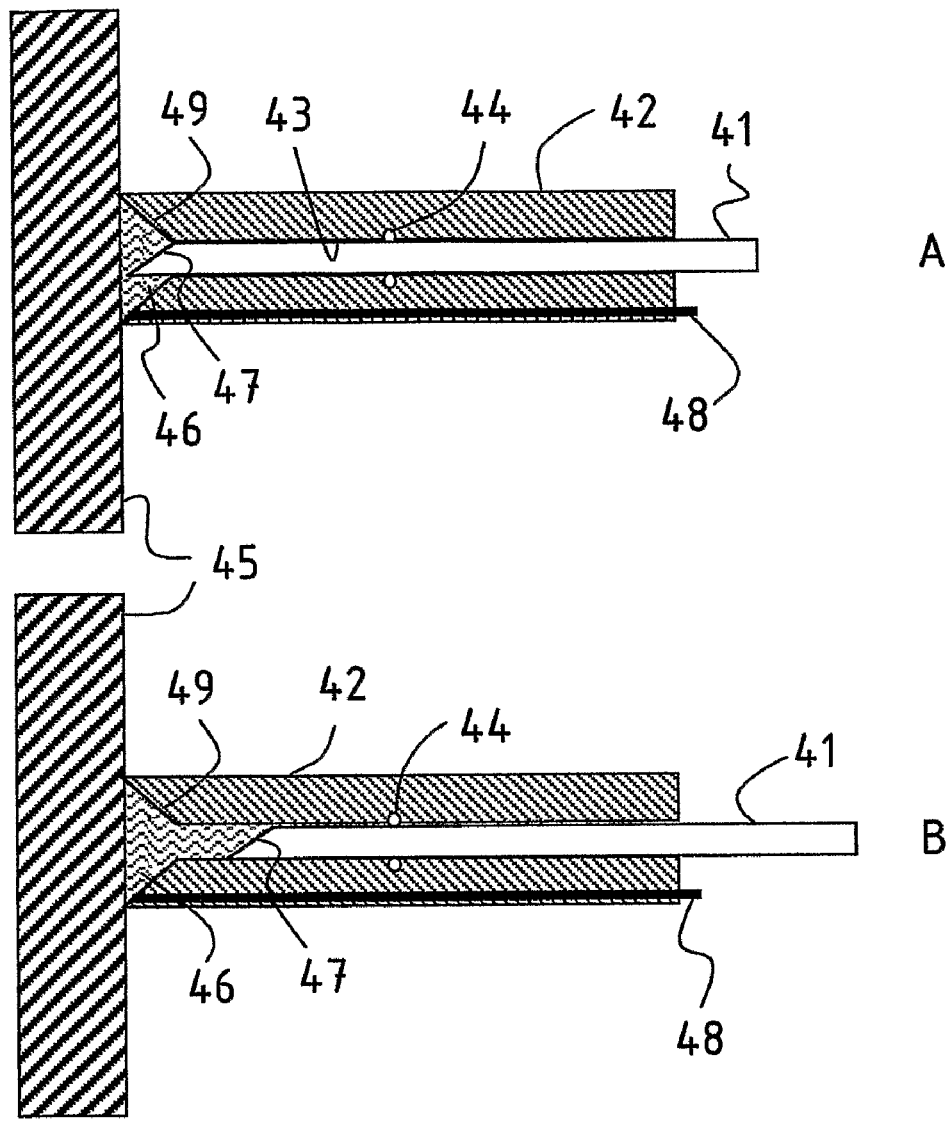
FIG. 4 is a schematic cross-sectional view of a device according to an embodiment of the present invention incorporating electrodes to detect and monitor the sample fluid during operation of the device.

An example of the use of sensing to provide feedback control is shown in FIG. 4 (showing two configurations, A and B). The lancet piston 41 is made of conductive material or has a conductive track incorporated within it such that the lancet piston can act as an electrode. This drawing shows the lancet piston 41 with an off-axis point 47 to illustrate that different points can be employed, but this is not material to the present embodiment. The housing 42 of the bore 43 incorporates a second electrode 48. The electrodes 41 and 48 are included in an electrical or electronic circuit (not shown) such that the presence or absence of a fluid 46 between the electrodes may be determined. For example, the presence of a conducting fluid may be detected by measuring an electrical current flowing from one electrode to the other. The use of fixed electrodes to determine the presence of fluid is well known in the general art of fluid level measurement. The present invention offers an important improvement for body fluid sampling by making the lancet piston a moving electrode whereby the conductive path between the two electrodes can only be maintained if the fluid sample maintains unbroken contact with the lancet piston as it moves up the bore. By so doing, it is possible with the invention to detect the presence of fluid before commencing the sample-taking step (FIG. 4 configuration A), and to further track the presence of or absence of fluid in the channel throughout the entire sampling process (FIG. 4 configuration B). By monitoring the conductivity it is possible to determine if the channel is being filled (for example, that there are no air bubbles or pockets of partial vacuum) and therefore to allow the user or system to be informed and take remedial action.

The present invention may be incorporated into a system so that the user can be alerted by a visible, audible or vibratory or other signal of the presence of sufficient sample for the intended analysis, before commencing the transport of the sample to the analysis chamber. Furthermore, the progress of the transport of the sample up the bore can be continuously monitored and the user can be further alerted that sufficient sample has arrived at the analysis chamber. A similar feedback and monitoring system can be employed for automated feedback control that eliminates the need for user involvement and improves the confidence that successful take-up and transport of the sample to the analysis chamber has occurred. FIG. 4 also illustrates that features can be incorporated in the device to keep the wound open or to hold the device off the skin for example by a shaped end or stand-off 49 to the housing at the forward end of the bore. It is possible that the stand-off may indent the skin surface, causing the skin to bulge up into the space enclosed by the stand-off 49. In such cases, the lancet may not have to extend beyond the stand-off to penetrate the skin successfully. This is well known in the prior art relating to alternative site testing.

Figure 5:
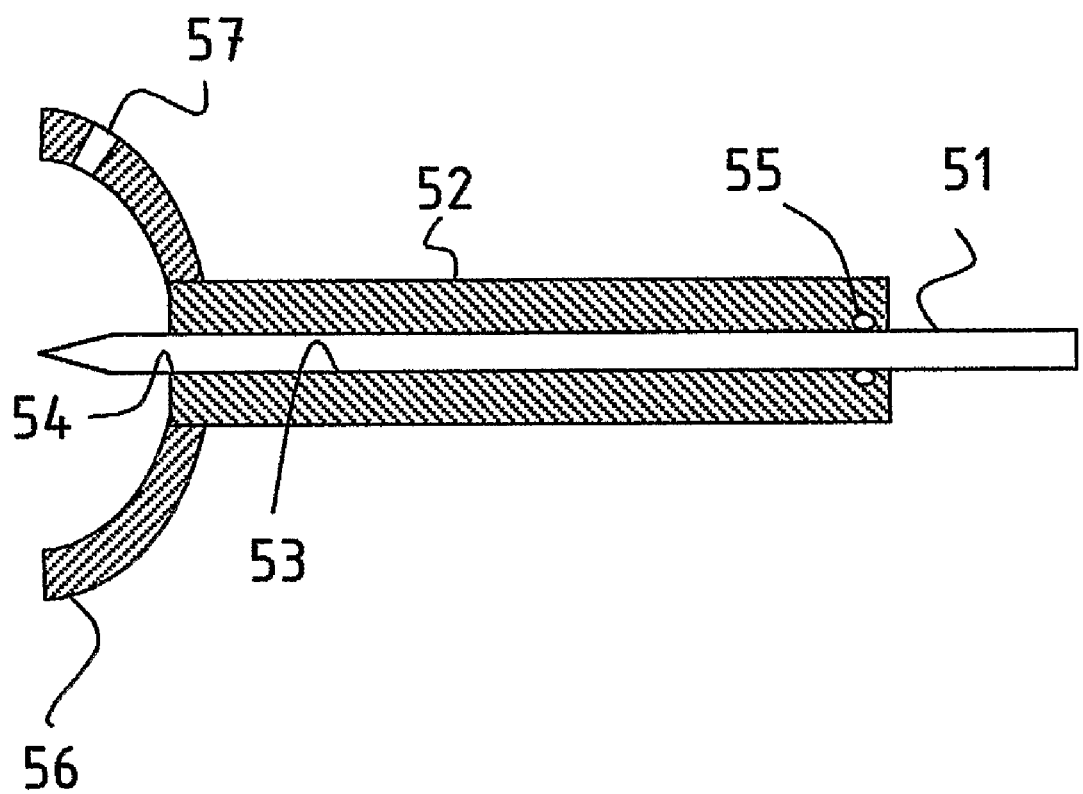
FIG. 5 is a schematic cross-sectional view showing a device according to an embodiment of the present invention incorporating a spacer member holding the end of the bore off the skin.

The invention may incorporate a spacer member or stand-off to hold the forward end of the bore off the skin. FIG. 5 illustrates the device of FIG. 1 equipped with a stand-off 56 joined to the housing 52. The stand-off holds the forward end 54 off the bore 53 of the skin (not shown) in use. The lancet piston 51 is extended beyond the end of the stand-off to penetrate the skin. A vent hole 57 is provided to allow air to enter the stand-off as the lancet piston is retracted to prevent a vacuum being generated through the movement of the lancet piston in relation to the bore 53 and rod seal 55. The stand-off 56 may be constructed from a transparent plastic or other transparent material to allow the user to see the blood drop forming and successfully bridging the gap between the skin and the forward end 54 of the bore 53 before allowing aspiration of the sample into the bore by retraction of the lancet piston 51.

A disadvantage of the embodiment in FIG. 5 is that a relatively large drop of blood needs to form to bridge the gap between the forward end of the bore and the skin, and this could lead to the stand-off being wetted with blood or other fluid.

Figure 6:
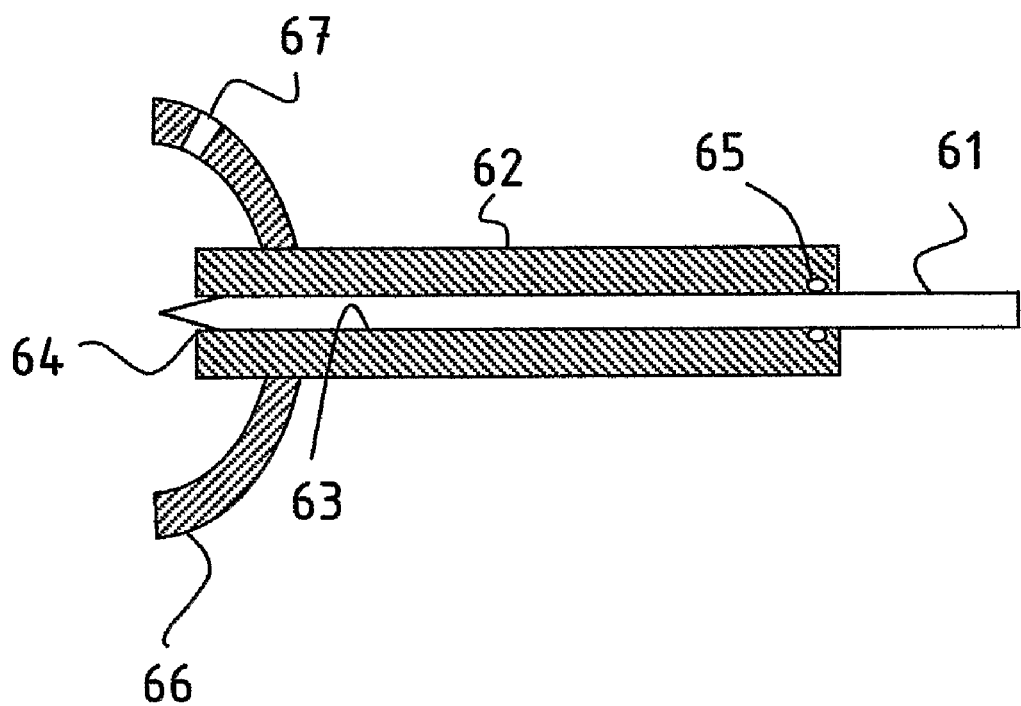
FIG. 6 is a schematic cross-sectional view showing a device according to an embodiment of the present invention incorporating a stand-off holding the end of the bore close to the skin, but not in contact with it.

FIG. 6 illustrates a modification of the embodiment of FIG. 5 wherein the forward end 64 of the bore 63 projects into the stand-off 66 to limit the distance fluid will have to bridge before it can be aspirated. A vent hole 67 is provided to allow air to enter the stand-off as the lancet piston is retracted to prevent a vacuum being generated in the stand-off 66 through the movement of the lancet piston in relation to the bore 63 and rod seal 65.

Another benefit of the invention over capillary sampling is the ability to drive fluid back out of the bore if, for example, an air bubble has formed in the bore, and to draw a fresh sample back in. The invention is able to take a second or subsequent sample with the same channel. This is not possible with a capillary without blowing the first sample back out by an external means. The invention can also eject the whole sample or a metered fraction out to waste or to another system without recourse to an external means (such as a wick) for drawing the sample out.

Capillary sampling generally requires that the whole capillary, to the point where the sample is to be delivered to, be filled with liquid. The described embodiments of the present invention are capable of delivering a slug of sample fluid to a desired location without the need to fill the whole channel. This can be achieved by purposely drawing air or other fluid in behind the initial sample as the lancet piston is retracted. This is not possible in capillaries with long parallel-bore channels. Thus the invention allows for the realisation of devices where a minimal sample of lower volume than the volume of the whole channel can be delivered to a chamber for measurement even if this chamber is some distance from the opening of the channel. This is an important benefit to the subject where it is desirable to take the smallest possible blood or other body fluid sample that is sufficient for the intended analysis to be performed.

Figure 7:
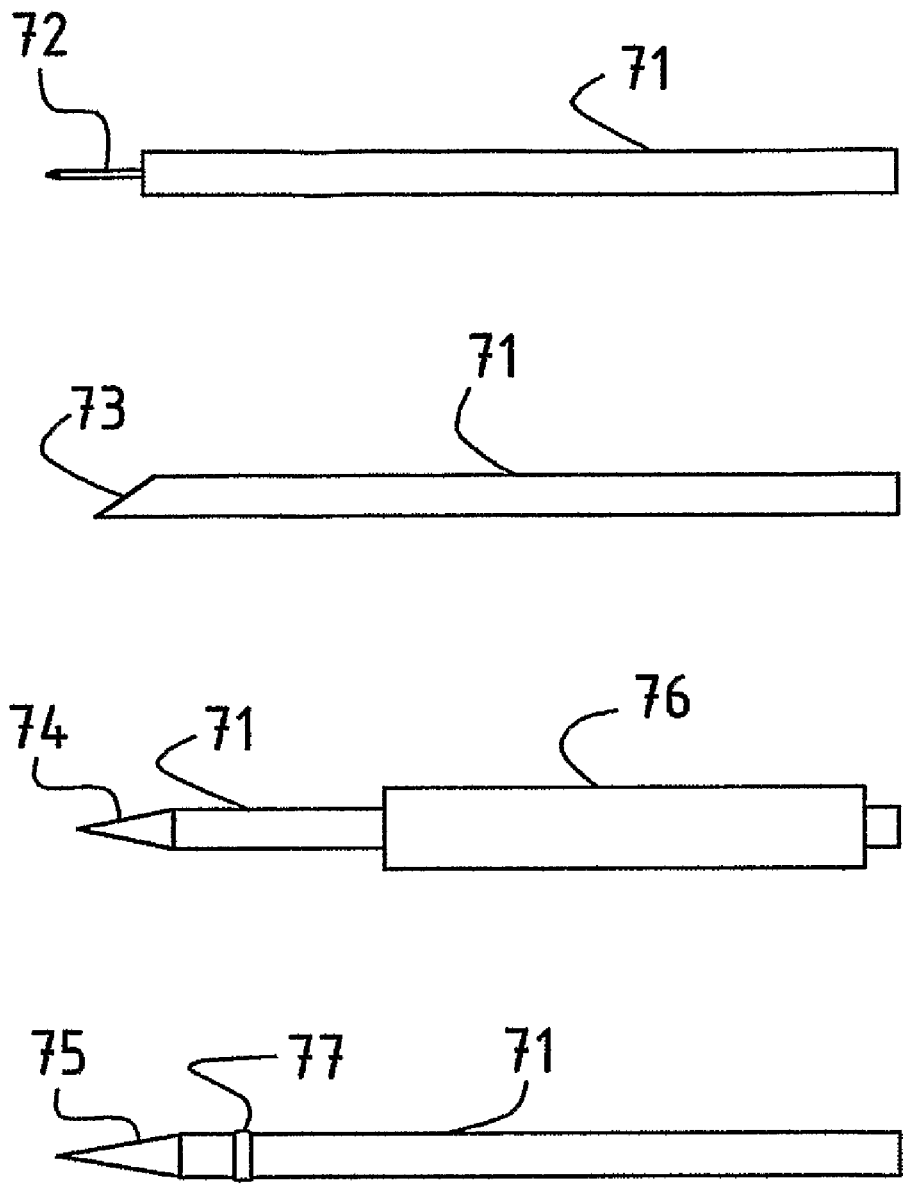
FIG. 7 is a side view of examples of lancet pistons for use in embodiments of the present invention, the lancet pistons having different sectional shapes along their longitudinal axes.

FIG. 7 illustrates four examples of lancet pistons 71 according to the present invention, having different external profiles and cross sections to provide alternative lancing points 72, 73, 74, 75 and one or more pistons 71, 76, 77 capable of sealing against the bore.

Yet another advantage of the described embodiments of the present invention is the ability to configure it continuously to pump an unlimited volume of fluid. The lancet piston/bore combination may be provided with known one-way valves (not shown) such that the operation of the lancet piston as a piston can pump fluid by reciprocation. With this arrangement, the swept volume of the lancet piston/bore combination need only be a fraction of the desired sample size, allowing for further miniaturisation.

It is also possible to use the invention to deliver fluids, e.g. prior to skin puncture. For example, a liquid anaesthetic may be packaged in the bore ahead of the lancet piston. As the lancet piston is driven out to puncture the skin the anaesthetic will be driven out onto the skin at the site to be punctured. The invention may also be used to deliver fluid to a site already punctured by the lancet piston. For example, the lancet piston may be driven out to puncture the skin and then retracted within the bore. A fluid, for example an anticoagulant, may be introduced into the bore in front of the lancet piston and this fluid forced into the wound by driving the lancet piston back down at least part of the bore. It is also possible to combine an anaesthetic and anticoagulant fluid and have these compounds delivered simultaneously to the intended puncture site on the skin, before puncturing the skin.

Figure 8:
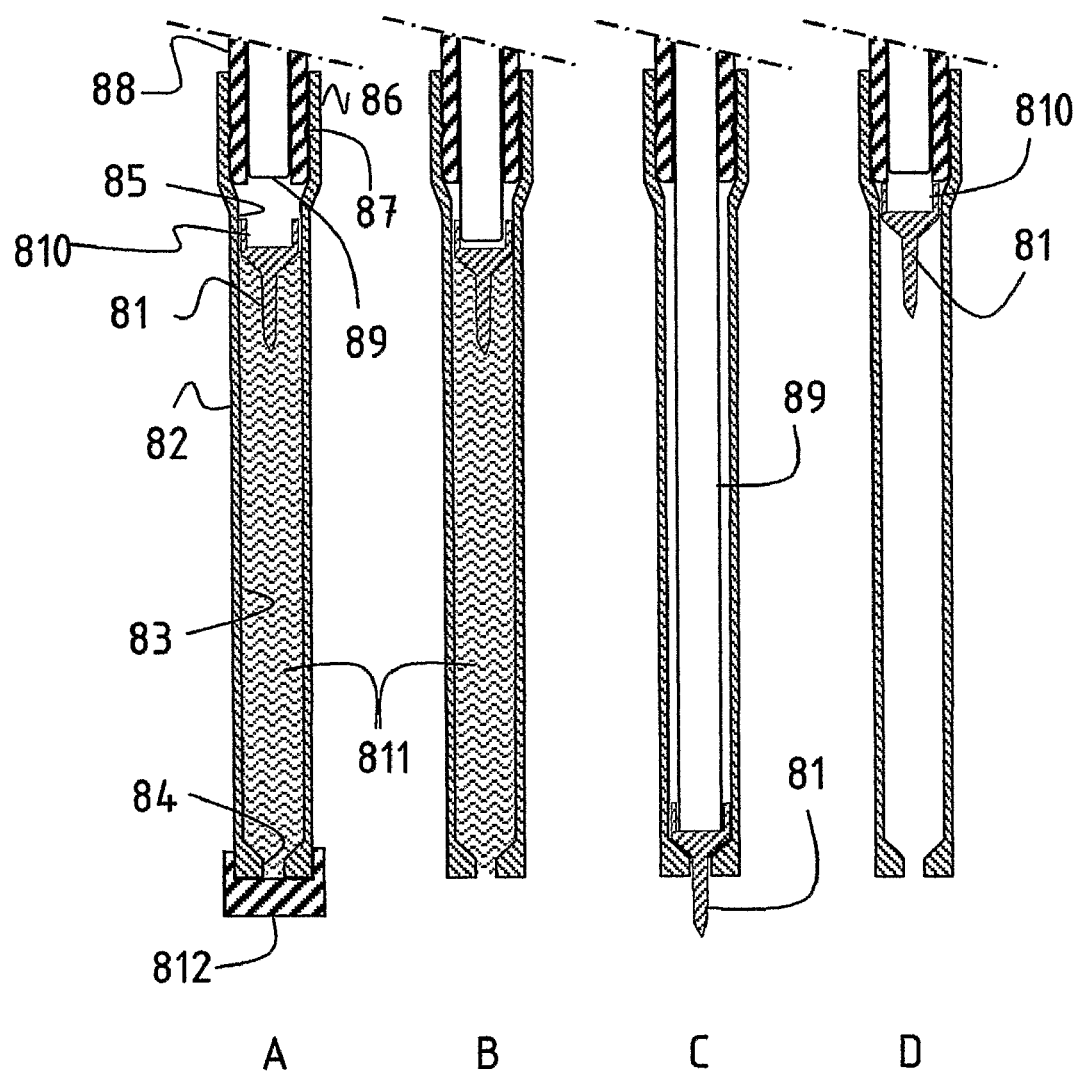
FIG. 8 is a sectional view of an embodiment of the invention particularly suited to the delivery of fluids to the skin before piercing the skin.
Figure 9:
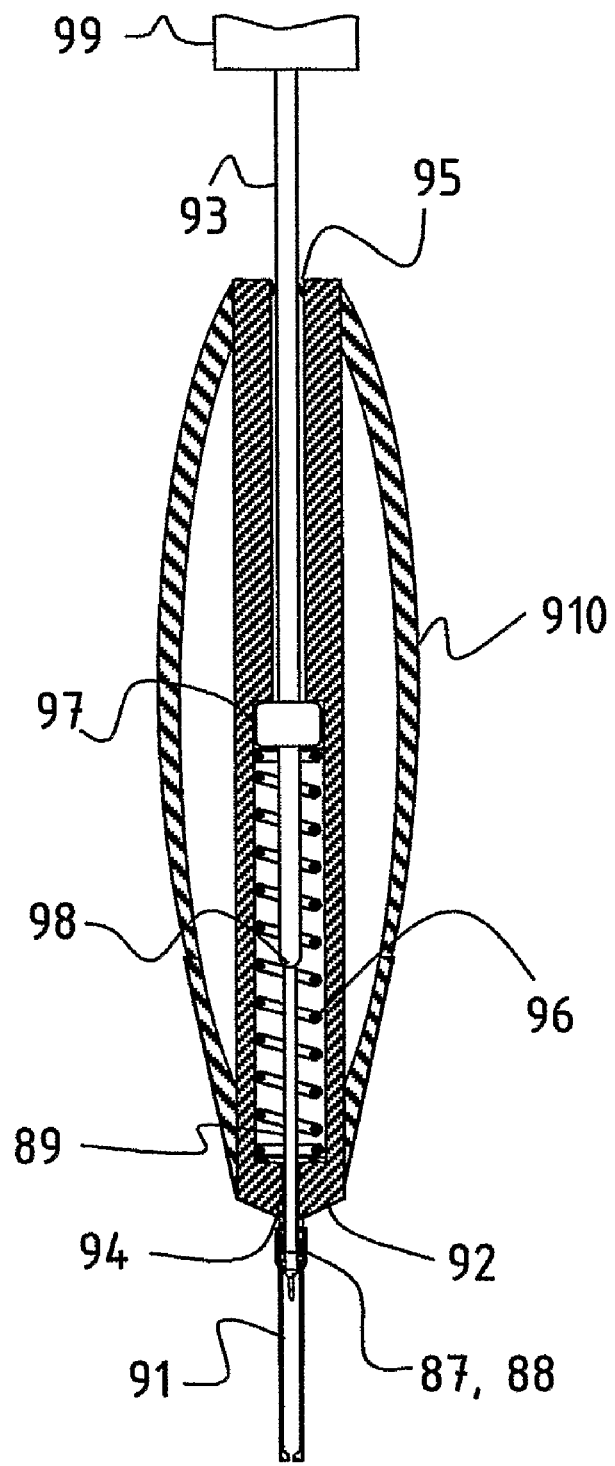
FIG. 9 is a sectional view of an apparatus to drive a device according to an embodiment of the present invention in use.

FIG. 8 illustrates one embodiment of the invention that is particularly suited to the delivery of fluid to the skin before puncture of the skin through the dispensed fluid. The device consists of a lancet piston 81 housed in a bore 83 within a housing 82. The whole of the housing 82 and lancet piston 81 represents a disposable (single use) device for aspirating and dispensing fluid and piercing the skin. The lancet piston 81 can be constructed of a single material as illustrated, or may be an assembly or single part consisting of a lancet portion, piston seal and plunger (not shown). The lancet piston 81 has a socket 810 at its rearmost end and is contained within a bore 83 in the housing 82. The forward end 84 of the bore 82 is reduced in diameter to provide an end-stop to limit forward travel of the lancet piston 81. The rearward end of the housing 86 incorporates a snap-fit feature 87 to connect with the forward end 88 of an apparatus for driving the lancet piston. Only the forward end of the apparatus is shown here. The complete apparatus is shown in FIG. 9. The snap-fit at the rearward end 86 of the housing 82 could equally be a press-fit, twist lock or other fixing. Configuration A shows the device before use, with the bore forward of the lancet piston filled with a fluid 811 for delivery to the skin. A removable cap 812 retains the fluid, preferably in a sterile condition, before use. In configuration B the cap 812 has been removed and a push-rod 89 inside the apparatus 88 is extended and engages with the socket 810 in the rear of the lancet piston 81. Further extension of the push-rod drives the lancet piston 81 down the bore 83, expelling the fluid 811. Configuration C shows the lancet piston at the forward end 84 of the bore 83 with the tip of the lancet piston 81 projecting to puncture the skin. At this point the push-rod 89 push-fits into the socket 810 of the lancet piston 81 if it has not already done so. Retracting the push rod 81 carries the lancet piston 81 back up the bore 83 until it comes to rest against the forward end of the apparatus 88. Configuration D illustrates further withdrawal of the push-rod 89 to release the lancet piston 81 in a safe position, protecting users from needle-stick injuries. The housing 82 containing the lancet piston 81 may now be detached from the forward end of the driving apparatus 88 and discarded.

FIG. 8 is intended to illustrate one embodiment of an apparatus-and-device combination. The features for connecting the lancet piston and bore housing to the apparatus can be of any suitable form, for example push fittings, snap fittings, collets, mechanical clutches, twist-lock fittings or any of the many connection fittings found in the arts of medical devices and laboratory pipettors.

It can be appreciated that the device of FIG. 8 is also capable of aspirating a liquid. To do this, the push-rod 89 is fully extended as at configuration C to engage the lancet piston 81. The forward end 84 of the bore 83 may then be immersed in a liquid and the push-rod 89 retracted to a position approximating configuration D. This action will fill the bore with liquid 811. The fluid may be delivered to the skin by reversing the push-rod 89 to expel the fluid. The device of FIG. 8 may also be used to pierce the skin and aspirate a blood sample. Starting from configuration D the lancet piston 81 is driven down the bore to configuration C to pierce the skin. At this point the lancet piston 81 can be retracted slightly so that the piercing point of the lancet piston 81 is recessed just inside the forward end 84 of the bore 83 (position not shown). Once a droplet of blood has formed on the skin, the forward end 84 of the bore 83 may be immersed in the blood droplet and a sample of blood may be aspirated by further withdrawing the lancet piston 81.

In this particular example the forward end 84 of the bore 83 has a reduced diameter to act as a dead-stop. If the device of FIG. 8 were designed to dispense 50 microliters, for example, the bore 83 would usefully be of the order of 2 mm in diameter and length of around 20 mm overall. Sweeping the lancet piston 81 along 17 mm of the length of the bore would then give a displaced volume of approximately 53 microliters. This 17 mm stroke is compatible with thumb-operated devices. If the embodiment were to be designed for a larger volume or shorter stroke, the reduced diameter at the forward end 84 of the bore 83 would provide a nozzle to retain liquid in the bore through surface tension. As previously stated, the aperture at the forward end of the bore ideally should be in the range 0.1 to 5 mm ID, preferably in the range 0.2 to 3 mm ID to prevent liquid leaking from the bore under the influence of gravity in use. The piercing point of the lancet piston 81 must be of smaller OD than the ID of the forward end 84 of the bore 83 to be able to pass through it, preferably without sealing onto the forward end of the bore or generating significant friction through contact with the forward end of the bore. Clearly, the forward end deadstop 84 may be configured on its outer surface to provide a stand-off feature to collect blood, as shown in FIGS. 5 and 6.

FIG. 9 illustrates a cross-section through a hand-held apparatus to drive the device of FIG. 8 through the steps of aspirating, dispensing and piercing. For ease of explanation, the rearward end of the apparatus is toward the top of FIG. 9. The apparatus consists of an inner casing 92 enclosing a compression spring 96. A push-rod 93 passes down through the inner casing 92 and is guided by a rearward guide 95 and a forward guide 94, both of these guides providing a low-friction sliding fit. The rearward end of the pushrod 93 is fitted with a thumb button 99. A spring seat 78 is attached to the push-rod 93 and slides freely within the inner casing 92. When the thumb button 99 is depressed the forward end 89 of the push-rod 93 is projected beyond the forward end 88 of the inner casing 92 and the sliding spring seat 97 compresses the spring 96 against the inner casing 92. Forward motion of the push rod 93 is limited by the step in diameter 98 in the push-rod 93, being larger than the diameter of the forward push-rod guide 94. Releasing pressure on the thumb button 99 allows the push rod 93 to retract under spring pressure, the sliding spring seat 97 acting against the inner casing 92 to provide a back-stop to limit rearward travel of the push-rod 93. An outer casing 910 is provided to enable the apparatus to be held easily in the hand.

The apparatus is intended to drive lancet piston/bore devices such as that illustrated in FIG. 8 through the steps of aspirating, dispensing and lancing or any combination of some or all of these steps. FIG. 9 shows a device 91 according to FIG. 8, being the combination of a housing and lancet piston (FIG. 8, features 82 and 81). The device 91 in FIG. 9 is shown at about actual size, whereas the same device in FIG. 8 is shown greatly magnified for clarity. The device 91 is fitted onto the forward end 88 of the inner casing 92 by way of a snap-fit feature 87 or other suitable fixing. Depressing and releasing the thumb button 99 in the apparatus of FIG. 9 performs all of the actions illustrated in FIG. 8 and described in relation to FIG. 8.

It can readily be appreciated that the apparatus of FIG. 9 could be equipped with adjustable forward and rearward dead-stops to adjust the depth of penetration of the lancet piston and to adjust the aspirate/dispense volume. For example, adjusting the limit of the forward travel of the forward end 89 of the push-rod 93 would adjust the depth of penetration of the lancet piston point. Adjusting the limit of the rearward travel of the forward end 89 of the push-rod 93 would adjust the swept volume of the device. It can readily be appreciated that the embodiment of the invention illustrated in FIG. 8 together with the apparatus of FIG. 9 can be adapted to allergy tests. The bore may be filled with allergen or a suspension of allergen particles in a carrier fluid, control fluid or suspension by aspiration either during manufacture (and sealed in the bore), at the point of use from a bulk container or bottle containing allergen, or at the point of use from a transfer station or well which has been pre-filled with a small amount of test solution or suspension from a bottle of allergen.

Figure 10:
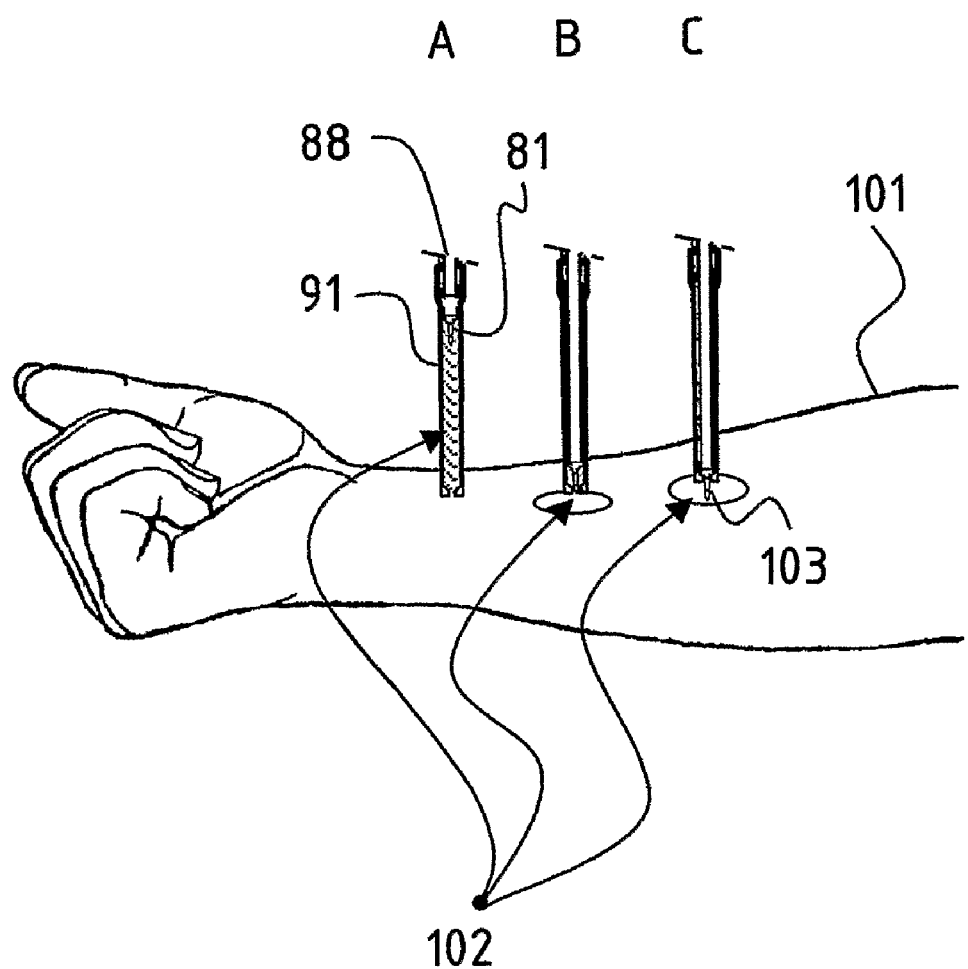
FIG. 10 illustrates three steps in the use of the device of FIG. 8 with the apparatus of FIG. 9 for allergy testing.

An example of how the present invention is to be used for allergen testing is illustrated in FIG. 10. The device 91 is the same as that of FIG. 8. For ease of illustration it is not to scale with the patient's arm. It is fitted onto and operated by the apparatus of FIG. 9. For ease of illustration, only the forward part 88 of the apparatus from FIG. 9 is shown. The operation is as follows:

The bore of the device 91 is filled with allergen 102 by the method described previously. Alternatively, if the device 91 has been pre-filled with allergen solution as in FIG. 8 configuration A, then remove the end cap shown in FIG. 8 as feature 812;

FIG. 10 sequence A: Place the forward end of the device 91 adjacent to the skin 101 so that the lancet piston 81 is held near-perpendicular to the skin surface 101;

FIG. 10 sequence B: Dispense the allergen sample 102 onto the skin 101 by depressing the thumb button on the apparatus shown in FIG. 9 as feature 99;

FIG. 10 sequence C: Continue with further forward movement of the thumb button to extend the lancet piston 81 beyond the end of the bore device 91 such that the tip 103 of the lancet piston 81 passes through the dispensed allergen sample 102 and punctures the skin 101;

The sequence is completed by releasing thumb pressure on the apparatus (feature 99 in FIG. 9), withdrawing the lancet piston 81 so that the lancet piston tip 103 is safely re-housed in the bore, and removing the whole device 91 from the skin surface 101 to leave the allergen sample 102 on the skin surface at the puncture site (not shown).

The device may incorporate a stand-off at the forward end of the bore as shown in FIGS. 5 and 6 to space the end of the bore slightly off the skin surface and allow the dispensed allergen to form a sessile drop on the skin surface that can be lanced through to a predetermined depth to cause damage to the underlying skin in the presence of the allergen. For such prick tests, it is not necessary to lance deeply enough to cause blood to spontaneously exude from the puncture wound. The intent is merely to damage the integrity of the skin surface in the presence of an allergen.

This embodiment can be adapted so that an end cap, plug or other seal may be punctured by the lancet piston tip or ruptured or detached by hydraulic pressure in the fluid caused by the initial movement of the piston before the lancet piston emerges from the end of the bore, to dispense the allergen sample contained in the bore, thus eliminating the need for a separate operation to remove the seal. This end cap or seal may also serve as a sterile barrier during storage of the device.

The present invention offers an improvement over the prior art allergy testing devices because accurate volumes of fluid may be aspirated and dispensed by virtue of the positive displacement principle. The invention also provides a means of pre-packaging fluids within a sealed bore for transport and storage before being delivered to the skin. It is envisaged that the present invention could be configured as a disposable lancet piston device driven by a re-usable hand-held lancing/pipetting drive system, such as that shown in FIG. 9.

Microneedle devices in the prior art are able to deliver fluids beneath the skin, but are not designed to deliver fluid to the skin before lancing in applications such as allergy testing. Microneedles could be employed to deliver fluid to the skin surface, however in such an application the microneedle would need to be of greater OD than the equivalent lancet piston. The microneedle would also have to be exposed during fluid deposition, whereas in the present invention the lancet piston tip is only exposed at the final piercing stage and is safely enclosed thereafter.

Figure 11:
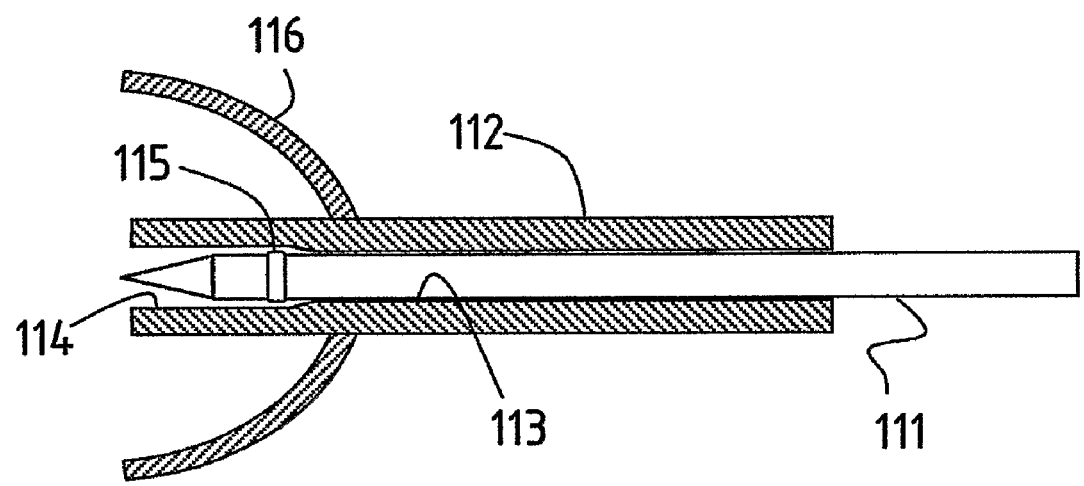
FIG. 11 illustrates an embodiment of the invention to minimise the friction of the lancet piston and having a piston seal.

Conventional lancets are typically accelerated to high speed thus ensuring good penetration into the skin and lower pain for the user. The high-speed operation helps to overcome the viscoelastic deformation of the skin and to minimise the time taken for the incision. Many commercial lancing devices seek to limit the mass of the lancet to enable it to be accelerated rapidly with moderate force to prevent bruising or other injury on impact. FIG. 11 illustrates an embodiment of the invention wherein the lancet piston 111 has a region of increased diameter 115 forming a piston seal. This is housed within a region of increased diameter 114 of the bore 113 towards the forward end of the bore. At this initial position, the lancet piston 111 is loosely guided in the bore 113 without appreciable friction and without sealing occurring at any point in the bore. The lancet piston 111 can be accelerated outwards to extend the point of the lancet piston rapidly beyond the forward end of the bore to lance or puncture the skin. During this lancing operation, the lancet piston 111 does not seal onto the bore 113, 114. This gives very low friction between the lancet piston and bore and because the mass of the lancet piston is small, it can be driven by conventional means such as springs, electromechanical actuators or other suitable known drive mechanisms to generate a high impact velocity when the lancet tip pierces the skin. The lancet piston travel may then be reversed such that the region of increased diameter 115 on the lancet piston is drawn back through the region of increased bore diameter 114 and further into the narrower section of the bore 113. At this point the region of increased diameter 115 on the lancet piston forms a piston seal in the bore 113 to assist in drawing fluid into the bore. Thus the embodiment benefits from low mass and low friction for the piercing operation, followed by a good seal (and thus higher friction) for aspirating and dispensing fluids. The region of increased diameter in the bore 114 serves to contain the lancet point at rest when attached to a lancing device, for example, of the type shown in FIG. 9, or a similar actuating device. The lancet piston may also be withdrawn further into the bore such that the region of increased diameter 115 on the lancet piston is drawn a small distance into the narrow section of the bore 113. This serves to hold the lancet piston in place when the lancet piston/bore assembly is not connected to a lancing device (for example, when packaged before use). This illustration incorporates an optional stand-off 116 to hold the forward end of the bore 114 at a determined small distance off the skin.

The key feature of this embodiment is the region of increased diameter on the lancet piston. When this region is inside the enlarged diameter section 114 of the bore, the lancet piston can move with low friction. It follows that a variation of this embodiment is to dispense with the region of increased diameter 114 in the bore completely and allow the region of increased diameter of the piston to protrude beyond the end of the bore during the lancing operation.

Figure 12:
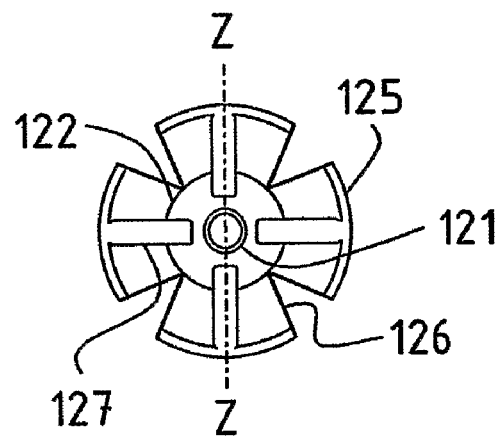
FIG. 12 illustrates an end view and sectional view of an embodiment of the invention combining the low friction feature shown in FIG. 11 with a stand-off designed to bring fluid to the end of the bore.
Figure 12:
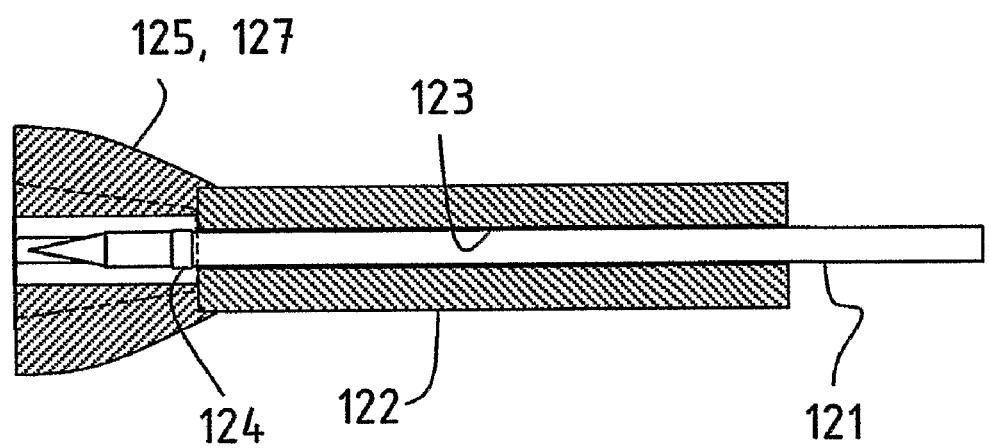

This principle is also compatible with the provision of a stand-off designed to draw blood to the forward end of the bore as shown in FIG. 12 in end view (A) and sectional view (B) (taken along center line Z-Z of A). The region of increased diameter 124 of the lancet piston 121 can extend beyond the forward end of the bore 123 without contacting the stand-off 125 and whilst being shielded by the stand-off against risk of accidental sharps injury to the user. The stand-off 125, contains four internally projecting fins 127 and slots 126 radially arranged around the bore 123 (only one fin and one slot is labelled for clarity) that assist in ensuring that the fluid sample which accumulates on the skin following the lancing step is encouraged to fill the space within the stand-off and immediately around the lancet and to contact the forward end of the bore. The purpose of the fins 127 in the stand-off is to subdivide the capillary space in the stand-off to make it easier for the sample to be transported against the effect of gravity to the forward end of the bore, and the slots provide venting to prevent a vacuum from forming in the stand-off during the aspiration stroke that transports the sample into the bore 123 by further rearward movement of the lancet piston.

Figure 13:
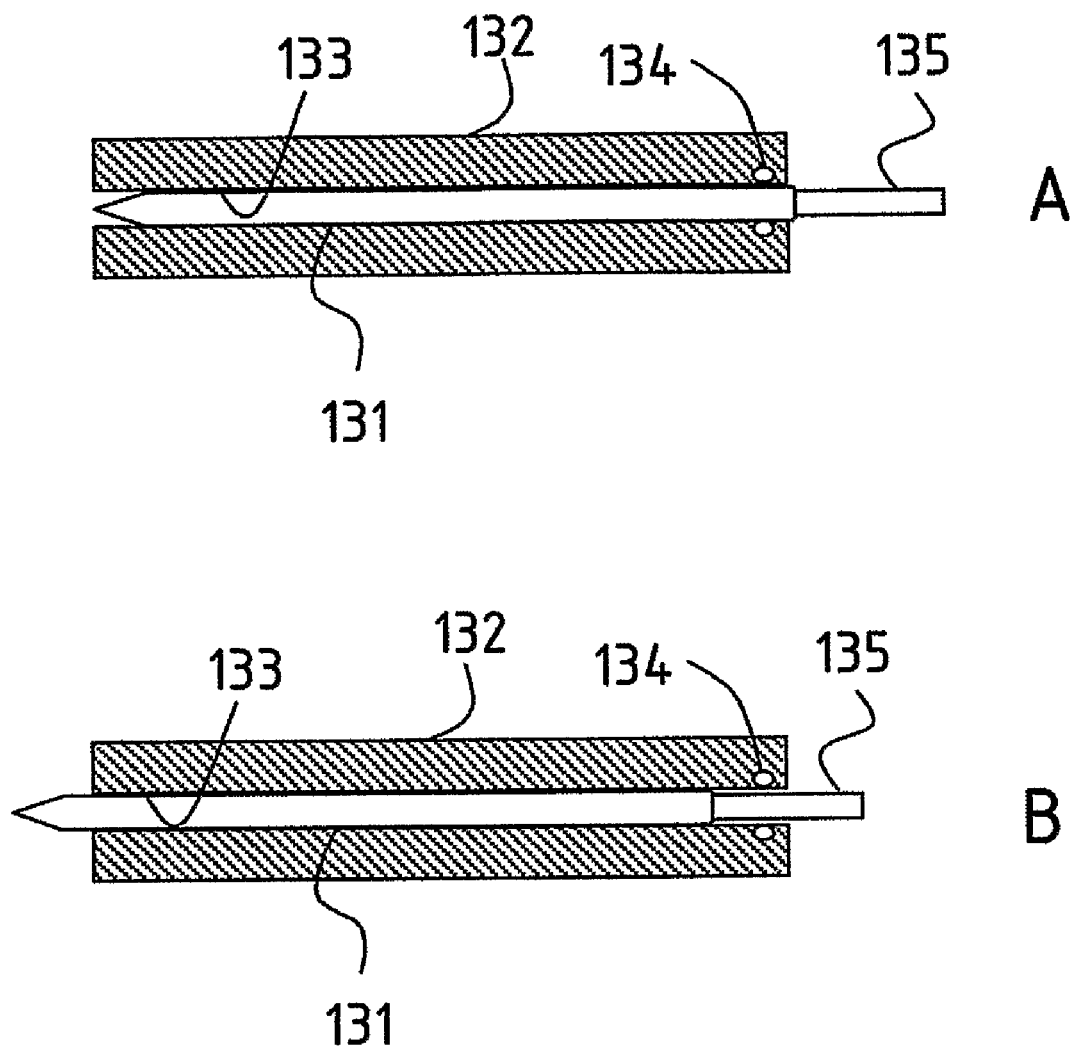
FIG. 13 illustrates an embodiment of the invention to minimise the friction of the lancet piston and having a rod seal.

FIG. 13 illustrates an alternative low-friction device. A lancet piston 131 is housed in a bore 133 in a housing 132. The rearward end of the bore 133 is provided with a rod seal 134. The lancet piston 131 is provided with a region of smaller diameter 135 at the rearward end of the lancet piston. In configuration A the rod seal acts against the major part of the lancet piston 131, sealing it in the bore 133. In configuration B the lancet piston 131 is moved forward such that the piercing point of the lancet piston 131 is extended beyond the forward end of the bore 133. The region of decreased diameter 135 on the lancet piston cannot seal against the rod seal 134. The lancet piston 131 and bore 133 dimensions are chosen to ensure a free sliding fit at position B. In this embodiment, the lancet piston is sealed against the bore in configuration A (relatively high friction), but is not sealed and runs with lower friction for the lancing operation (configuration B).

Figure 14:
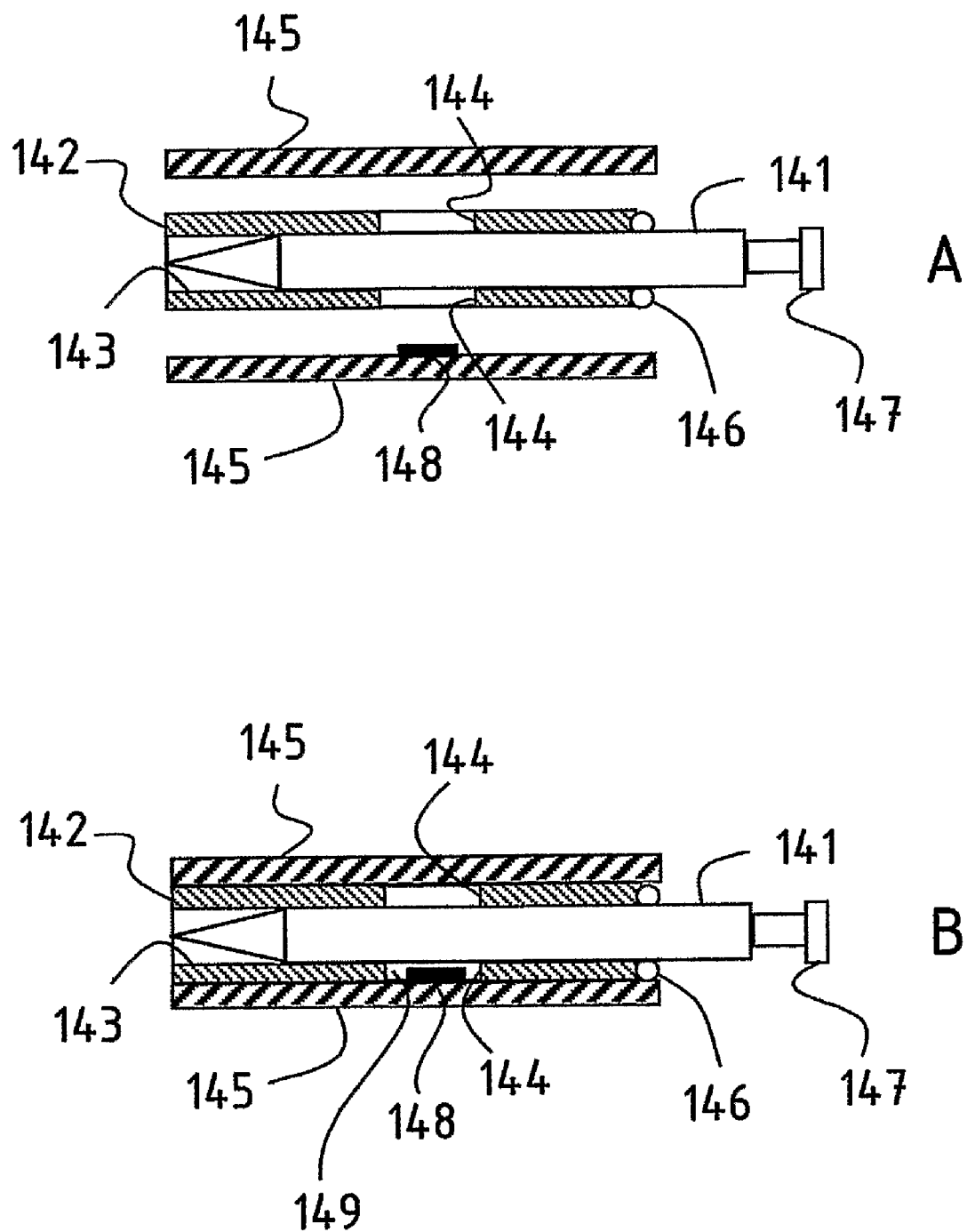
FIG. 14 shows exploded (A) and assembled (B) sectional side views of a three-layer embodiment of a device according to an embodiment of the present invention.

The devices of these embodiments of the invention may be readily integrated with blood glucose and other test strips and point-of-care instruments. FIG. 14 illustrates an exploded view (A) and assembled view (B) of one way in which the invention may be integrated with a test strip. The bore 143 forms part of a housing 142 (shown in section) which is provided with a through-hole 144 (to form a chamber 149 when the device is assembled). The bottom and top of the device is capped with a cover or laminate 145. One or both of these laminates may incorporate a sensor 148 or electrodes or a chemical or biological test in the region of the through-hole 144 and thus chamber 149. Such sensors or electrodes or chemical tests may usefully be printed or coated onto the laminates. The through-hole may also form an optical reading path. A rod seal 146 seals the lancet piston 141 within the assembly. The three layers are assembled to form a test strip with integrated lancet piston 141. The lancet piston is provided with a feature 147 to enable the lancet piston to be gripped by an actuation mechanism. In use, a fluid sample may be drawn into the bore 143 and further into the sensor chamber 149 for analysis. This embodiment is compatible with the method of manufacture of glucose tests strips and other analyte test strips while providing the benefits of integrated lancing and positive displacement fluid handling.

Figure 15:
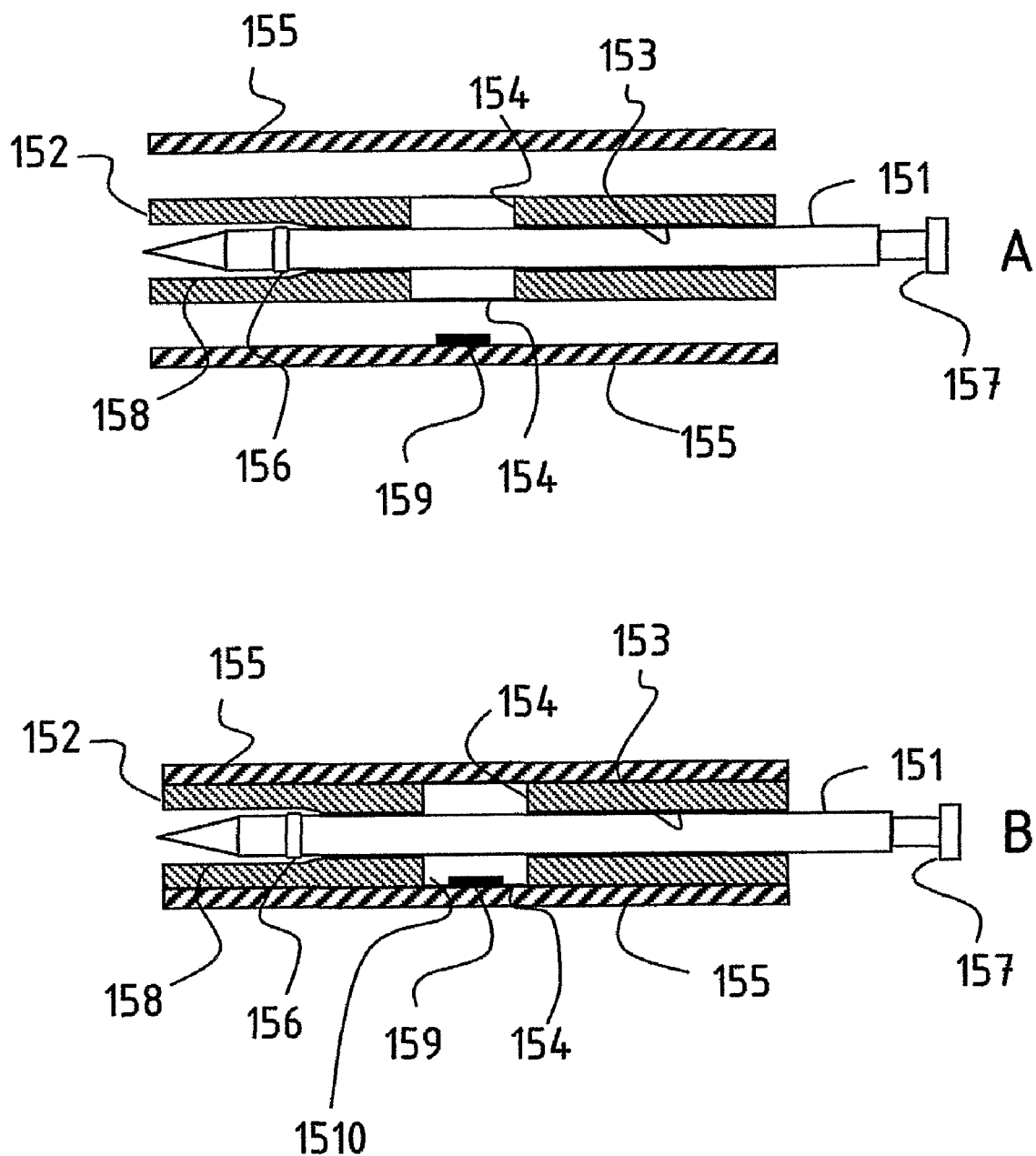
FIG. 15 shows exploded (A) and assembled (B) sectional side views of a three-layer embodiment of a device according to an embodiment of the present invention, incorporating features from FIG. 11.

FIG. 15 illustrates another example of how the invention may be integrated with a test strip and includes the feature for low-friction lancing illustrated in FIG. 11. The lancet piston 151 is provided with a region of increased diameter at the forward end of the bore 156 to provide a piston seal. The bore 153 in the housing 152 is provided with a region of increased diameter 158 such that the lancet piston seal 156 is a loose fit in the forward end of the bore 158, at the position it occupies in the bore just before the lancing operation is initiated. The lancet piston 151 is provided with a feature 157 to enable the lancet piston to be gripped by an actuation mechanism. A through-hole 154 becomes a chamber 1510 when the assembly is completed by the addition of the top and bottom layers 155 (FIG. 15 B). As described for the assembly in FIG. 14, sensors 159 or test elements may be incorporated in one or more of the laminates 155. In this embodiment, a piston seal 156 provides the seal between the bore 153 and the lancet piston 151 when the lancet piston is withdrawn such that the piston seal 156 enters the narrower section of the bore 153. In use, a fluid sample may be drawn into the bore 153 and further into the sensor chamber area 1510 for analysis. This embodiment is compatible with the method of manufacture of glucose test strips and other analyte test strips, while providing the benefits of integrated lancing and positive displacement fluid handling.

Figure 16:
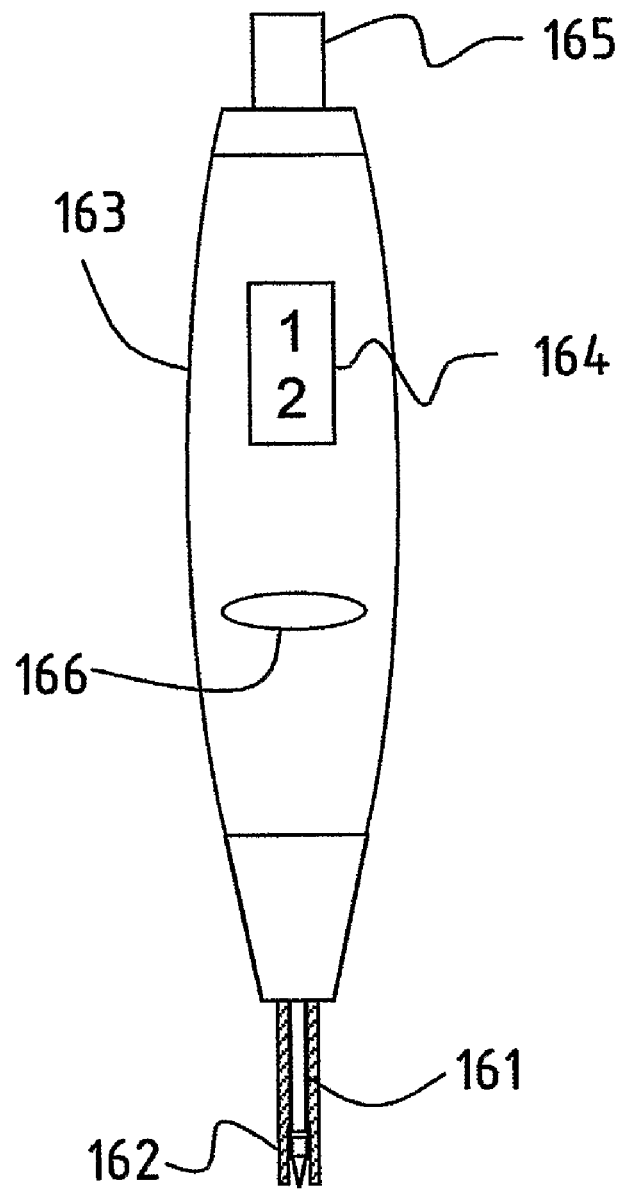
FIG. 16 is an illustration of a sampling/dispensing/lancing apparatus for use with and incorporating an embodiment of the invention.

The invention may be configured for the sole purpose of taking a fluid sample from the skin and transferring some or that entire sample to a container or external system for analysis. FIG. 16 illustrates a hand-held apparatus according to the invention consisting of a lancet piston 161 in a housing 162 that contains the bore (said lancet piston/housing combination being shown in sectional view) combined with a lancing/pipetting device 163 that drives the lancet piston/bore combination to perform both the lancing and pipetting functions of the invention. This device 163 may incorporate electrically-driven, spring, manual, pneumatic, hydraulic or other drive mechanisms for both accelerating the lancet piston to pierce the skin and to drive the lancet piston back and forth within the bore to aspirate and dispense fluids.

The apparatus may incorporate a push/pull button 165 to cock the lancing mechanism and/or to control the pipetting function (for example, by thumb pressure) and/or a trigger button 166 to fire the lancet mechanism or engage an electronic control system to do so. Such a device may be provided with a thumbwheel or other system 164 to set the desired aspirate/dispense volumes by controlling the extent of travel of the lancet piston within the bore by adjustment of dead-stops or by controlling a motorised or electromagnetic actuator as known in the prior art relating to pipettors. This volume-setting system may be manual or electronic. It may also incorporate features to limit the depth of penetration of the lancet tip into the skin, for example by the known methods of adjusting internal dead-stops to limit the stroke of the lancet tip, and/or by adjusting the projection of the stand-off relative to the lancet tip. The apparatus may also control the force applied to the lancet piston. For clarity, only two digits corresponding to these possible controls are shown. The apparatus may be equipped with an electronic display and controls to set and run programs to allow the user to choose optimum settings for a particular sampling operation, as known in the prior art relating to electronic pipettors and electronic lancing devices.

Figure 17:
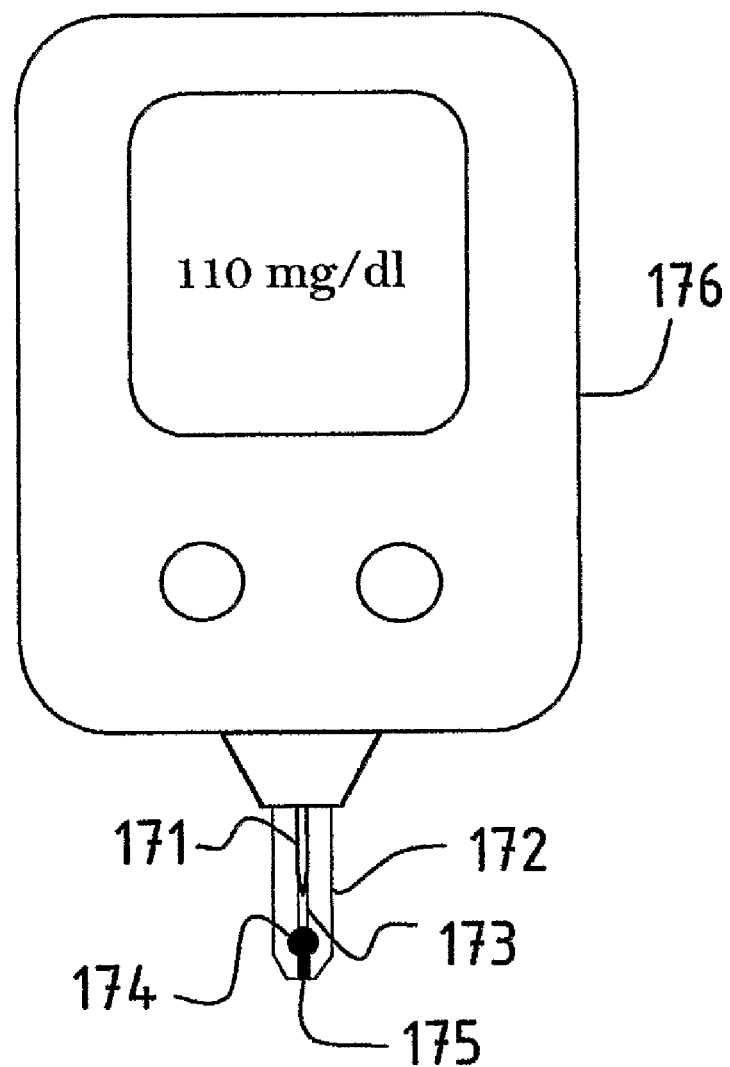
FIG. 17 is an illustration of an embodiment of the invention integrated with a Point of Care meter system.

The lancet piston/bore assembly is preferably disposable and capable of being picked up and ejected semi-automatically in the manner of a disposable pipette tip on a pipettor. The stand-off components that contact the skin, such as shown in FIGS. 5, 6, 11 and 12, are also preferably disposable, and are preferably (but not necessarily) integrally formed with the housing and bore during manufacture FIG. 17 illustrates how integrated test-strip embodiments of the invention such as those illustrated in FIGS. 2, 3, 14, 15 and 18 may be integrated with a point-of-care testing device such as a blood glucose monitor. A test strip 172 is provided with a bore 173, lancet piston 171 and chamber 174. The chamber incorporates an analytical chemistry or method for example to measure blood glucose concentration. The POC meter 176 contains a manual, spring-powered, pneumatic powered, hydraulically powered or electrically-powered mechanism for driving the lancet piston in both lancing and sampling modes and a means of reading the test on the test strip. The whole forms a single integrated system capable of piercing the skin, aspirating a sample of blood or other fluid 175 into the chamber 174, reading the test strip result and reporting a diagnostic value to the user.

From one viewpoint, the embodiments of the invention combine features of lancing and pipetting. Known pipetting devices are intended solely to aspirate and dispense liquids. Known blood sampling devices are intended to acquire a sample and perhaps to integrate such sample acquisition with some form of measurement.

Preferred embodiments of the invention incorporate a lancet tip specifically to pierce the skin, a method and mechanism to drive a lancing operation (in addition to a pipetting function), features to ensure low mass and low friction during the lancing step, and chambers or test-strip chemistry for integrated analysis.

Preferred embodiments of the present invention offer an advantage over known capillary-based sampling devices because the lancet functions as a piston, thus being capable of generating higher pressure differential for moving fluid than is possible with capillaries. Furthermore, the preferred embodiments also offer the advantages that:

- controlling the displacement and speed of the lancet piston with respect to the bore closely controls the fluid sample transport within the bore;
- fluid samples can be transported across variations in the cross-section of the sampling conduit or bore with ease;
- fluid contained in the fluid-containing space may be ejected on demand;
- air bubbles within the sampling conduit or bore can be detected, accommodated and/or ejected;
- repeat sampling is possible with the same sampling conduit or bore;
- feedback control of sample volume and integrity is provided for.

Furthermore, the preferred embodiments of the present invention may be seamlessly integrated with sensors, analysis chambers, associated automation and/or system controls, and feedback to the user.

Using a lancet piston to make the incision provides an advantage over known devices employing hollow microneedles because microneedles have to be of larger OD than the lancet piston of the present invention for the same diameter of sampling conduit. This is because the sampling conduit runs up the center of the microneedle and therefore the microneedle has an OD greater than the ID of the sampling conduit, whereas the lancet piston of the present invention runs within the sampling conduit and is thus of equal OD to the ID of the conduit.

The preferred embodiments of the present invention also offer advantages over known devices that employ air pressure behind a diaphragm to drive a lancet and take a sample. For example US2003/0088191 does not incorporate a piston seal, elongate sampling conduit or analysis chamber. The use of a diaphragm driven by air and the compressibility of the air headspace can make it very difficult to exert close control over the sampling and dispensing volumes when compared with the positive displacement principle used in the preferred embodiments of the present invention.

The preferred embodiments of the present invention exhibit advantages over known devices that employ suction to draw blood to the surface of an incision. Such devices cannot aspirate a blood sample and have no provision for doing so. They are also distinguished in that the end of the bore is of sufficient ID to surround a droplet of blood on the skin with the preferred aim of avoiding contact between the droplet of blood and the device. In order to aspirate a sample, the devices of the preferred embodiments of the present invention should have a bore aperture or nozzle of small enough diameter to be fully bridged by the liquid sample such that it is wetted around the entire circumference of the aperture by the fluid sample. Typically, it is also necessary to employ an aperture to the bore of sufficiently small diameter (preferably within the range described above) to ensure that liquid within the bore is retained by surface tension forces when the bore is withdrawn from the fluid. Known devices of the suction type cannot aspirate a sample because they possess an aperture to the bore intentionally larger than the diameter that would otherwise be necessary to allow contact between the fluid sample and the circumference of the bore. They further have no means to dispense a fluid and no integral chamber for analysing a sample.

Many suction devices also differ from the preferred embodiments of the present invention in that the piston is fully retracted before the blood sample collects on the skin, and the system is sealed to the skin. In that case, the blood sample is surrounded by a partial vacuum and has no access to atmospheric air. This has the disadvantage that the sample may be out-gassed. The suction is lost when the device is removed from the skin to allow access to the droplet.

Embodiments of the invention will now be further described with reference to reduced-to-practice examples:

EXAMPLE 1

A device according to an embodiment of the present invention was fabricated by Cambridge Product Development Ltd (Huntingdon, Cambridge, England).

Figure 18:
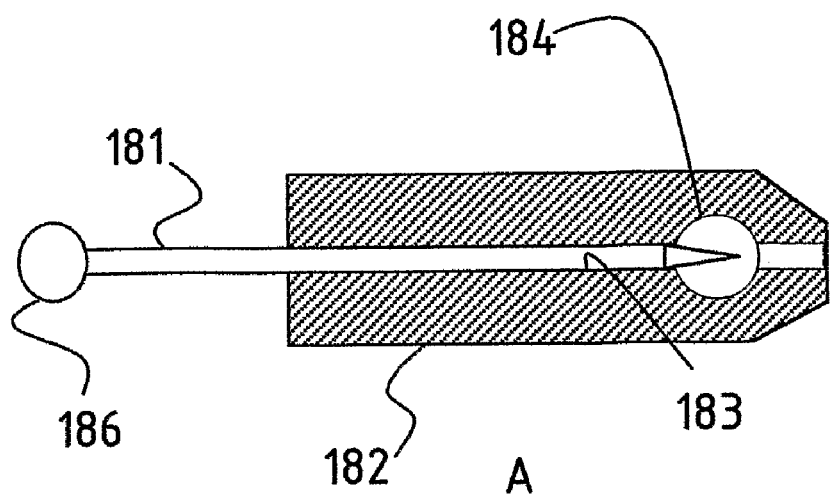
FIG. 18 shows plan sectional views of a device according to an embodiment of the invention comprising a lancet piston, bore and chamber as set out in Example 1.
Figure 18:
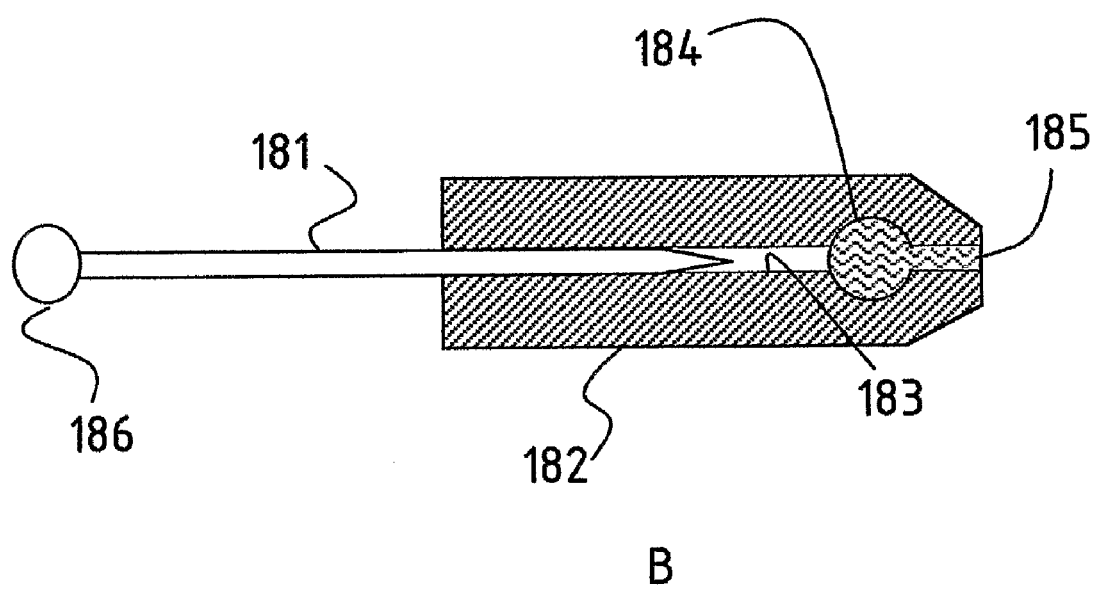

With reference to FIG. 18 (plan view), the device consists of a housing 182 of 2 cm length and 5 mm width incorporating a 0.67 mm diameter bore 183. A chamber 184 of 2 mm diameter×0.5 mm (approximately) high is connected to the bore. The position of this chamber is approximately 3 mm from the forward end of the bore. It can be appreciated that if this chamber were positioned at the forward end of the bore the fluid would be drawn directly into the chamber before any section of the bore. A lancet piston 181 of 0.67 mm OD and 32 mm length overall is inserted into this bore with the lancet point orientated towards the chamber end of the device. The lancet piston is provided with a feature 186 to enable the lancet piston to be gripped more easily. The volume of the bore is approximately 0.35 microliters per mm length and the volume of the chamber approximately 1.6 microliters (within the range of size for sensor chambers in commercially available blood glucose test strips). Withdrawing the lancet piston 181 some 5 mm beyond the chamber 184 is theoretically sufficient to displace all the air from the chamber and fill it with fluid.

Figure 19:
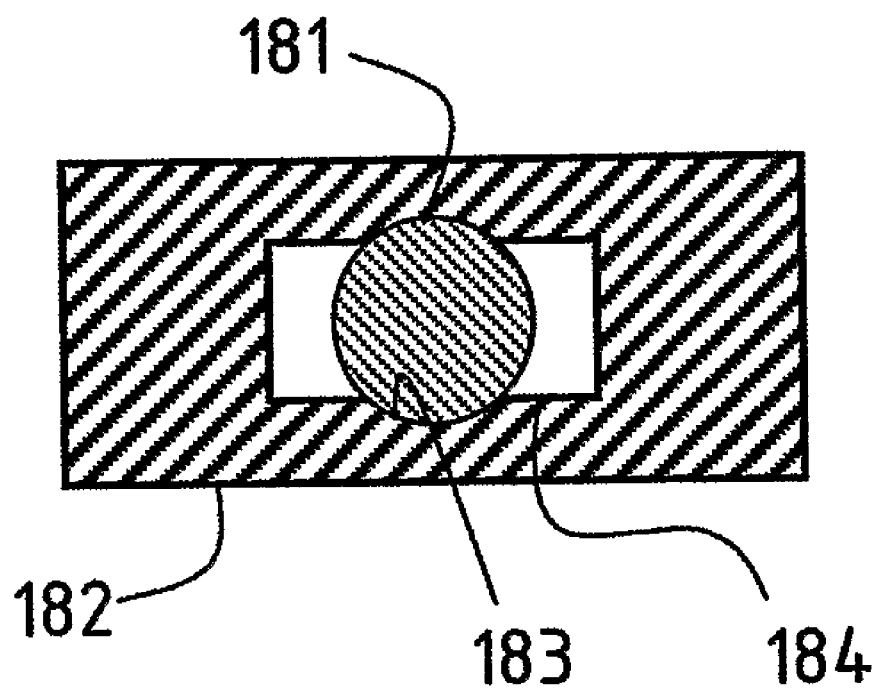
FIG. 19 is a cross-sectional end view of the device shown in FIG. 18.

FIG. 19 shows a sectional right hand elevation of the device (not to scale). The lancet piston 181 is housed in a bore 183 incorporating the chamber 184.

The device may be constructed by a conventional process of using a removable forming tool to form a bore in a plastic body (in this case low density polyethylene) into which a piston (in the present case a lancet piston) is inserted after the forming tool is removed. One embodiment of the invention may usefully be constructed by adapting the method of WO01/12329, the entire content of which is hereby incorporated by reference. The plunger therein can be replaced by a lancet piston, with the bore formed around the lancet piston itself instead of a removable tool. This gives a commercial advantage in that there is no need for a removable tool and the alignment and insertion of a lancet piston to replace the forming tool.

The device of this Example was tested initially with aqueous ink. The device is transparent, allowing the movement of liquid and air to be directly observed therein. As expected, if the lancet piston were driven fully home in the bore before a liquid sample was aspirated, the liquid would wet the tip of the lancet piston. When the lancet piston was withdrawn beyond the chamber, the liquid was drawn in behind as expected, and remained in contact with the lancet piston throughout, The liquid did not initially fill the chamber, but instead bridged the center of the chamber in line with the bore, forming two air bubbles in the chamber on each side of the center line. This was due to the low surface energy of polyethylene, which is not ideal for wetting by an aqueous liquid. This was overcome by varying the mode of operation of the device.

In a variation of this first method, the liquid was drawn in beyond the chamber and then the forward end of the bore was removed from the liquid. The lancet piston was further withdrawn so that air was drawn in behind the liquid until the meniscus at the end of the slug of liquid farthest from the lancet piston was within the chamber. Reversing the travel of the lancet piston pushed liquid back down the bore and the air ahead of the liquid was pushed out of the chamber, resulting in the chamber being entirely filled with liquid. This process was repeated several times and gave the same result each time.

In a second method, illustrated in the FIGS. 18A and 18B, the lancet piston 181 was withdrawn until the tip was within the chamber 184 (FIG. 6A) before the forward end of the bore was offered to the liquid. The lancet piston 181 was then further withdrawn to aspirate liquid 185 (FIG. 18B). Due to the fact that there was no liquid 185 in contact with the lancet piston tip, the air was drawn out of the chamber 184 and the chamber was completely filled with liquid 185.

If required, the wetting out of the chamber may be enhanced by altering the surface energy of the lancet piston, chamber or both either by choice of materials or surface treatment.

In all cases, all of the liquid or a desired aliquot is ejected from the device by driving the lancet piston back towards the forward end of the bore.

Two identical devices were then tested on a volunteer. The lancet piston was flame sterilised before being inserted into the device with the lancet point set approximately 5 mm beyond the end of the bore. The lancet piston tip was then driven into a finger to create a pinprick wound. Blood was drawn into the device by withdrawing the lancet piston into the bore according to the second method of operation above. No difference was observed in the behaviour of blood in the device when compared with the observations of aqueous ink. The blood did not clot within the short timescale of the experiments.

This Example demonstrates many of the advantageous features of the embodiment, including lancing, sample taking, sample ejection, withdrawal of air from a chamber, filling a chamber with fluid, movement of liquid, air, or both together and safe housing of the lancet piston tip after use.

It was observed that small aliquots of liquid as discrete "slugs" could be drawn into the bore and moved back and forth at will. These aliquots could be bounded by air (or other fluid) at each end, or could be in contact with the lancet piston at one end and air (or other fluid) at the other. Thus, a small aliquot may be drawn into the bore and delivered to any section along it. This is not possible with a capillary unless the bore is tapered, stepped down, or is treated to incorporate a surface energy gradient, both methods being limited in their practical application and being incapable of being reversed without application of an external force.

It was also observed that the lancet piston position could be used to control capillarity in bores that are of sufficiently small diameter (such as the present example). The lancet piston is first withdrawn into the bore some distance from the forward end of the bore, with the bore open to air. If the forward end of the bore is now immersed into liquid, and if the fluid is capable of wetting the bore, some liquid will enter the bore under capillary forces. The air in the bore between the lancet piston and the liquid is sealed. There is no vent present as there would be with a capillary-fed device. If the bore surface is capable of being wetted with blood or other body fluids being tested, liquid will only enter the bore until the pressure of the trapped air in the bore comes to equilibrium with the capillary pressure driving the liquid. This can be used to control precisely how much liquid enters the bore under capillarity (the distance the liquid travels along the bore), and when. If the lancet piston is subsequently moved, it can draw in or eject the sample. This can be used to control small volumes within the device.

The example also demonstrated that commercially available materials with a low surface energy such as olefinic plastics could be used successfully with the present invention.

EXAMPLE 2

A device according to an embodiment of the present invention may be fabricated by the following method.

A disposable syringe of 1 ml capacity (Becton Dickinson Plastipak) is adapted by first withdrawing the plunger rod completely and removing the rubber piston from the front end of the plunger rod. A counter bore of 1 mm diameter and 6 mm deep is drilled into the center of the front end of the plunger rod to accept a lancet tip.

A lancet tip is provided by cutting the plastic off a disposable "Softclix" lancet (Boehringer Mannheim) to recover a lancet of 0.75 mm diameter and 25 mm long with a ground lancet tip. The lancet is glued into the hole prepared in the front end of the plunger rod. The rubber piston is pierced through the center by the lancet, and is threaded along the lancet before being seated onto the end of the plunger rod. This results in the construction of a composite lancet piston with a piston seal. This assembly is inserted into the bore of the syringe to form a lancet piston device.

It can be readily appreciated that the lancet, plunger and piston form a lancet piston and could be of unitary construction, and that the piston/plunger combination could also be incorporated into a unitary construction if desired. The syringe barrel forms the bore and provides for a narrower bore nozzle at the luer end. This nozzle is of approximately 2.15 mm ID and helps to retain fluid by surface tension when the device is being handled with the end open to the atmosphere. The nozzle also aids in dispensing the test fluid to a small area. As previously stated, devices according to the preferred embodiments having smaller bores than approximately 2 to 5 mm diameter (such as in Example 1) may not need a nozzle. The length of the lancet and the depth of the counter bore are selected so that 7 mm of the lancet project beyond the luer fitting of the syringe when the plunger is pushed fully home.

The syringe may be filled with fluid (aqueous ink) to represent a fluid to be delivered, such as anaesthetic, antiseptic or allergen. A cap is provided to retain the fluid before use. This could equally be an interference-fit plug that could be pushed out by hydraulic pressure, or a welded thin film seal that could be ruptured or detached prior to or during use.

The device was filled with aqueous ink and held approximately 1 mm off the surface of an orange (to represent skin). Pushing the plunger down delivered the ink to the surface of the orange before the lancet piston tip pierced the skin of the orange. This example demonstrates the ability of the invention to deliver fluid to a site and then to pierce that site through the fluid in one operation. It can be readily appreciated that the device itself can be provided with a stand-off, an example of a stand-off 56 being illustrated in FIG. 5.

It is envisaged that the device could also be mounted in a lancing drive system that itself may provide a stand-off against the skin.

This Example embodiment has important application to the diagnosis and treatment of allergies, particularly if the device is scaled down from this Example 2 to a size and scale approaching that of the device of Example 1 and illustrated in FIGS. 8 to 10. Such a device would ideally deliver a volume of allergen solution in the range 1 to 50 microliters.

The invention claimed is:

1. An allergy-testing device, the device having a housing with a bore and a lancet slidably fitting in the bore, the lancet being a penetrating component and being movable between a puncture position, in which a sharpened tip of the lancet is exposed from a forward end of the bore for a puncture operation, and a retracted position, in which the lancet is rearwardly displaced along the bore to a safe position to protect users from needle-stick injuries, the device having seal means in sliding engagement with a sealing surface, one of the seal means and the sealing surface being fixedly movable with the lancet during forward and rearward displacement of the lancet, wherein in the retracted position a liquid-containing space is defined in the bore forwardly of the lancet tip, an aqueous liquid contained in the liquid-containing space comprising an aqueous solution of allergen or a suspension of allergen particles in a carrier liquid, the liquid-containing space having a cross-sectional diameter of 3 mm or less to allow aqueous liquid to fully bridge across the diameter of the forward end of the bore and wet the full circumference of the forward end of the bore and be aspirated into the liquid-containing space, and be retained in the liquid-containing space by surface tension forces and by the seal means, wherein the seal means is operable substantially to prevent flow of the aqueous liquid from the liquid-containing space past the seal means on forwards, and rearwards displacement of the lancet and to oppose dripping of the aqueous liquid from the forward end of the bore under the influence of gravity so that:
 (i) displacement of the lancet from the puncture position to the retracted position provides suction for drawing aqueous liquid into and along the liquid-containing space from the forward end of the bore, and
 (ii) displacement of the lancet from the retracted position to the puncture position provides pressure for expelling aqueous liquid from the liquid-containing space via the forward end of the bore;
 wherein the device further includes a spacer member located forwardly of the forward end of the bore, the spacer member being for contact with the skin of a subject, the spacer member including a vent which vents the spacer member and the forward end of the bore when the sealing means is in sealing engagement with the sealing surface and the spacer member is pressed against the skin of the subject;
 wherein the seal means is formed by the outer surface of the lancet, the sealing surface being an internal surface of the bore.

2. A device according to claim 1 wherein the outer surface of the lancet is profiled to provide the seal means as a surrounding projection.

3. A device according to claim 1 wherein the seal means is disposed adjacent the lancet tip, at least when the lancet is in the retracted position.

4. A device according to claim 1 having cooperating means for providing an intermediate delay position for the lancet between the puncture position and the retracted position.

5. A device according to claim 1 having at least one stop member for limiting the forward and/or rearward travel of the lancet.

6. A device according to claim 4 wherein, during retraction from the puncture position, the contacting or increased contacting of the seal means with the sealing surface provides the intermediate delay position.

7. A device according to claim 1 wherein the bore includes a region of increased cross-section dimension for location of the seal means or the sealing surface at the puncture position of the lancet.

8. A device according to claim 1 wherein the seal means or sealing surface is disposed beyond the forward end of the bore at the puncture position of the lancet.

9. A device according to claim 1 wherein the seal means is a sealing member disposed rearwardly in the device from the forward tip of the lancet and movable with the lancet tip and the sealing surface is formed by the internal surface of a sealing region of the bore.

10. A device according to claim 9 wherein a cross-sectional dimension of the sealing member is greater than a cross-sectional dimension of the liquid-containing space but less than or equal to 10 times the cross-sectional dimension of the liquid-containing space.

11. A device according to claim 1 wherein the lancet tip is sharpened to have a radius of curvature in at least one dimension of one quarter or less of the narrowest cross-sectional dimension of a non-tip region of the lancet.

12. A device according to claim 1 wherein, in use, the liquid-containing space presents means for measuring or testing a characteristic of the liquid to liquid contained in the liquid-containing space.

13. A device according to claim 1 having a secondary conduit from the bore, communicating with the liquid-containing space.

14. A device according to claim 1 having a closure member located forwardly of the lancet tip, sealing at least a part of the liquid-containing space.

15. A device according to claim 1 wherein the spacer member is dimensioned to provide an accumulation space between a puncture in the skin of the subject and the forward end of the bore.

16. A device according to claim l including sensing means for sensing the presence or absence of liquid at the forward end of the bore.

17. A device according to claim 16 wherein the sensing means includes at least two electrodes, at least one of which is located at the forward end of the bore to detect the presence or absence of liquid at the forward end of the bore by measurement of the resistance between the electrodes.

18. A device according to claim 17 wherein the lancet provides one of the electrodes.

19. A device according to claim 1 including sensing means for sensing the presence and/or amount of liquid along the liquid-containing space.

20. An allergy-testing device according to claim 1 wherein the liquid-containing space is pre-filled and sealed, the liquid-containing space being pre-filled with said aqueous liquid.

21. An allergy-testing device, the device having a housing with a bore and a lancet slidably fitting in the bore, the lancet being a penetrating component and being movable between a puncture position, in which a sharpened tip of the lancet is exposed from a forward end of the bore for a puncture operation, and a retracted position, in which the lancet is rearwardly displaced along the bore to a safe position to protect users from needle-stick injuries, the device having seal means in sliding engagement with a sealing surface, one of the seal means and the sealing surface being fixedly movable with the lancet during forward and rearward displacement of the lancet, wherein in the retracted position a liquid-containing space is defined in the bore forwardly of the lancet tip, an aqueous liquid contained in the liquid-containing space comprising an aqueous solution of allergen or a suspension of allergen particles in a carrier liquid, the liquid-containing space having a cross-sectional diameter of 3 mm or less to allow aqueous liquid to fully bridge across the diameter of the forward end of the bore and wet the full circumference of the forward end of the bore and be aspirated into the liquid-containing space, and be retained in the liquid-containing space by surface tension forces and by the seal means, wherein the seal means is operable substantially to prevent flow of the aqueous liquid from the liquid-containing space past the seal means on forwards and rearwards displacement of the lancet and to oppose dripping of the aqueous liquid from the forward end of the bore under the influence of gravity so that:
  (i) displacement of the lancet from the puncture position to the retracted position provides suction for drawing aqueous liquid into and along the liquid-containing space from the forward end of the bore, and
  (ii) displacement of the lancet from the retracted position to the puncture position provides pressure for expelling aqueous liquid from the liquid-containing space via the forward end of the bore;
  wherein the device further includes a spacer member located forwardly of the forward end of the bore, the spacer member being for contact with the skin of a subject, the spacer member including a vent which vents the spacer member and the forward end of the bore when the sealing means is in sealing engagement with the sealing surface and the spacer member is pressed against the skin of the subject;
  wherein the seal means is a sealing member disposed around the lancet, the sealing surface being an internal surface of the bore.

22. An allergy-testing device, the device having a housing with a bore and a lancet slidably fitting in the bore, the lancet being a penetrating component and being movable between a puncture position, in which a sharpened tip of the lancet is exposed from a forward end of the bore for a puncture operation, and a retracted position, in which the lancet is rearwardly displaced along the bore to a safe position to protect users from needle-stick injuries, the device having seal means in sliding engagement with a sealing surface, one of the seal means and the sealing surface being fixedly movable with the lancet during forward and rearward displacement of the lancet, wherein in the retracted position a liquid-containing space is defined in the bore forwardly of the lancet tip, an aqueous liquid contained in the liquid-containing space comprising an aqueous solution of allergen or a suspension of allergen particles in a carrier liquid, the liquid-containing space having a cross-sectional diameter of 3 mm or less to allow aqueous liquid to fully bridge across the diameter of the forward end of the bore and wet the full circumference of the forward end of the bore and be aspirated into the liquid-containing space, and be retained in the liquid-containing space by surface tension forces and by the seal means, wherein the seal means is operable substantially to prevent flow of the aqueous liquid from the liquid-containing space past the seal means on forwards and rearwards displacement of the lancet and to oppose dripping of the aqueous liquid from the forward end of the bore under the influence of gravity so that:
  (i) displacement of the lancet from the puncture position to the retracted position provides suction for drawing aqueous liquid into and along the liquid-containing space from the forward end of the bore, and
  (ii) displacement of the lancet from the retracted position to the puncture position provides pressure for expelling aqueous liquid from the liquid-containing space via the forward end of the bore;
  wherein the device further includes a spacer member located forwardly of the forward end of the bore, the spacer member being for contact with the skin of a subject, the spacer member including a vent which vents the spacer member and the forward end of the bore when the sealing means is in sealing engagement with the sealing surface and the spacer member is pressed against the skin of the subject;
  wherein the seal means is a sealing member disposed at the internal surface of the bore, the sealing surface being an outer surface of the lancet.

23. A device according to claim 22 wherein the seal means is a rod seal.

24. A method of operating an allergy-testing device, the device having a housing with a bore and a lancet slidably fitting in the bore, the lancet being a penetrating component and being movable between a puncture position, in which a sharpened tip of the lancet is exposed from a forward end of the bore for a puncture operation, and a retracted position, in which the lancet is rearwardly displaced along the bore to a safe position to protect users from needle-stick injuries, the device having seal means in sliding engagement with a sealing surface, one of the seal means and the sealing surface being fixedly movable with the lancet during forward and rearward displacement of the lancet, wherein in the retracted position, a liquid-containing space is defined in the bore forwardly of the lancet tip, the liquid-containing space having a cross-sectional diameter of 3 mm or less so that aqueous liquid fully bridges across the diameter of the forward end of the bore and wets the full circumference of the forward end of the bore and is aspirated into the liquid-containing space, and is retained in the liquid containing space by surface tension forces and by the seal means, wherein the seal means substantially prevents flow of the aqueous liquid from the liquid-containing space past the seal means on forward and rearwards displacement of the lancet and opposes dripping of the aqueous liquid from the forward end of the bore under the influence of gravity, the method including displacing the lancet between the puncture and retracted positions to carry out the following steps in sequence:
  (i) drawing aqueous liquid into and along the liquid-containing space from the forward end of the bore by suction, the aqueous liquid comprising an aqueous solution of allergen or a suspension of allergen particles in a carrier liquid, (ii) before puncturing the skin of a subject, expelling said aqueous liquid from the liquid-containing space via the forward end of the bore onto the skin of the subject at a skin location to be punctured, and (iii) puncturing the skin of the subject at the skin location to be punctured;

wherein the device further includes a spacer member located forwardly of the forward end of the bore, the spacer member including a vent, wherein in steps (ii) and (iii) the spacer member is pressed in contact with the skin of the subject and the vent vents the spacer member and the forward end of the bore when the sealing means is in sealing engagement with the sealing surface.

25. A method of operating an allergy-testing device, the device having a housing with a bore and a lancet slidably fitting in the bore, the lancet being a penetrating component and being moveable between a puncture position, in which a sharpened tip of the lancet is exposed from a forward end of the bore for a puncture operation, and a retracted position, in which the lancet is rearwardly displaced along the bore to a safe position to protect users from needle-stick injuries, the device having seal means in sliding engagement with a sealing surface, one of the seal means and the sealing surface being fixedly movable with the lancet during forward and rearward displacement of the lancet, wherein in the retracted position, a liquid-containing space is defined in the bore forwardly of the lancet tip, wherein an aqueous liquid is contained in the liquid-containing space comprising an aqueous solution of allergen or a suspension of allergen particles in a carrier liquid, the liquid-containing space having a cross-sectional diameter of 3 mm or less so that aqueous liquid fully bridges across the diameter of the forward end of the bore and wets the full circumference of the forward end of the bore and is retained in the liquid-containing space by surface tension forces and by the seal means, wherein the seal means substantially prevents flow of said aqueous liquid from the liquid-containing space past the seal means on forward and rearwards displacement of the lancet and opposes dripping of the aqueous liquid from the forward end of the bore under the influence of gravity, the method including displacing the lancet between the puncture and retracted positions to carry out the following steps in sequence:

(i) before puncturing the skin of a subject, expelling said aqueous liquid from the liquid-containing space via the forward end of the bore onto the skin of the subject at a skin location to be punctured, and (ii) puncturing the skin of the subject at the skin location to be punctured;

wherein the device further includes a spacer member located forwardly of the forward end of the bore, the spacer member including a vent, wherein in steps (i) and (ii) the spacer member is pressed in contact with the skin of the subject and the vent vents the spacer member and the forward end of the bore when the sealing means is in sealing engagement with the sealing surface.

* * * * *

UNITED STATES PATENT AND TRADEMARK OFFICE
CERTIFICATE OF CORRECTION

| | | |
|---|---|---|
| PATENT NO. | : 8,092,394 B2 | Page 1 of 1 |
| APPLICATION NO. | : 11/574919 | |
| DATED | : January 10, 2012 | |
| INVENTOR(S) | : Anthony David Harman et al. | |

It is certified that error appears in the above-identified patent and that said Letters Patent is hereby corrected as shown below:

In column 3, line 45, delete "5,369,047" and insert -- 5,368,047 --, therefor.

In column 17, line 58, delete "D." and insert -- B. --, therefor.

In column 22, line 54, delete "optimuin" and insert -- optimum --, therefor.

In column 22, line 64, delete "manufacture" and insert -- manufacture. --, therefor.

In column 25, line 17, delete "throughout," and insert -- throughout. --, therefor.

In column 27, line 51, in Claim 1, delete "forwards, and" and insert -- forwards and --, therefor.

In column 28, line 58, in Claim 16, delete "claim I" and insert -- claim 1 --, therefor.

In column 29, line 57, in Claim 22, delete "apuncture" and insert -- a puncture --, therefor.

In column 32, line 9, in Claim 25, delete "forward" and insert -- forwards --, therefor.

Signed and Sealed this
Thirteenth Day of March, 2012

David J. Kappos
*Director of the United States Patent and Trademark Office*